United States Patent
Kim et al.

(10) Patent No.: US 7,599,072 B2
(45) Date of Patent: Oct. 6, 2009

(54) METHOD FOR DETERMINING PHYSICAL PROPERTIES OF A MULTILAYERED PERIODIC STRUCTURE

(75) Inventors: Young Dong Kim, Seocho-Gu (KR); Jin Mo Chung, Nowon-Gu (KR); Seung Ho Han, Ansan-Si (KR)

(73) Assignee: University-Industry Cooperation Group of Kyung Hee University (KR)

( * ) Notice: Subject to any disclaimer, the term of this patent is extended or adjusted under 35 U.S.C. 154(b) by 36 days.

(21) Appl. No.: 12/070,717

(22) Filed: Feb. 20, 2008

(65) Prior Publication Data

US 2008/0297770 A1 Dec. 4, 2008

(30) Foreign Application Priority Data

| May 30, 2007 | (KR) | 10-2007-0052806 |
| Aug. 1, 2007 | (KR) | 10-2007-0077351 |
| Oct. 17, 2007 | (KR) | 10-2007-0104495 |
| Oct. 17, 2007 | (KR) | 10-2007-0104496 |

(51) Int. Cl.
*G01B 11/24* (2006.01)
*G01N 21/55* (2006.01)

(52) U.S. Cl. .................................. 356/601; 356/445

(58) Field of Classification Search ............. None
See application file for complete search history.

(56) References Cited

U.S. PATENT DOCUMENTS

| 6,741,335 | B2 * | 5/2004 | Kinrot et al. | 356/28 |
| 6,867,866 | B1 | 3/2005 | Chang et al. | |
| 7,283,225 | B2 * | 10/2007 | Onvlee et al. | 356/237.2 |

* cited by examiner

*Primary Examiner*—Michael P Stafira
(74) *Attorney, Agent, or Firm*—Lerner, David, Littenberg, Krumholz & Mentlik, LLP

(57) ABSTRACT

There is provided a method of calculating physical properties of a periodic structure. At least one physical property related to reflectivity or transmittance of a periodic structure is measured, and then, at least one physical property related to reflectivity or transmittance of a virtual periodic structure is calculated to obtain corresponding physical properties from the virtual periodic structure. The at least one calculated physical property is compared with the at least one measured physical property. When the virtual periodic structure is horizontally divided into a plurality of layers, at least three substances can have horizontally repeated periods in the middle layers of the divided structure. In accordance with an embodiment of the present invention, the microscopic formation of the periodic structure including a native oxide layer formed on the periodic structure or an intentionally formed surface coating layer thereon can be nondestructively and accurately tested.

9 Claims, 8 Drawing Sheets

US 7,599,072 B2

METHOD FOR DETERMINING PHYSICAL PROPERTIES OF A MULTILAYERED PERIODIC STRUCTURE

CROSS-REFERENCE TO RELATED APPLICATIONS

This application claims the benefit of Korean Patent Application Nos. 10-2007-0052806 filed on May 30, 2007; 10-2007-0077351 filed on Aug. 1, 2007; 10-2007-0104495 filed on Oct. 17, 2007; and 10-2007-0104496 filed on Oct. 17, 2007, the disclosures of which are hereby incorporated herein by reference.

BACKGROUND OF THE INVENTION

1. Technical Field

Embodiments of the present invention described herein relate to a method of testing a periodic structure, e.g., to determine a shape of a structure having a feature repeated in one or more dimensions, the method performed such as through non-destructive testing via measurement of reflectivity or transmittance.

2. Discussion of Related Art

Generally, to fabricate electronic devices, such as semiconductor devices or display devices, processes of cleaning, thin-film growing, photolithography and thin-film etching are repeated many times to produce the consumer products. For example, in the photolithography process, a circuit of a mask where an image to be fabricated is formed and is transferred to a photosensitive material (photo resist) to form a pattern, and the pattern is used as an etch barrier to form a desired circuit on a thin film.

In the semiconductor and display devices fabricated by using the photolithography process, the desired circuit needs to be transferred to the thin film in an accurate shape in each step. This is possible based on the accuracy of the photolithography process. That is, only when the shape of a desired pattern is accurately transferred to a photo resist, and the resist layer properly functions as the etch barrier, an accurate circuit can be formed on the thin film. That is, the accurate pattern is to be formed by the photo resist before the circuit is formed on the thin film, and this can be confirmed by a testing process.

To test a pattern, there has been generally used a method of optically observing a shape of a semiconductor device using a pattern tester, for example. However, since the resolution of the pattern tester can be insufficient for determining the shapes of "nano-level" patterns which measure only a few nanometers in length. Using a pattern tester, it is difficult to perform an accurate analysis. To solve such a drawback, in the semiconductor research and production line, there has been used a method of analyzing a specific shape using equipment such as an electron microscope.

However, when an electron microscope is used, since a section of a semiconductor device is to be cut for the analysis of a shape thereof, the semiconductor device as fabricated cannot be used again. Moreover, since the measurement is to be conducted under vacuum environment, it can take an excessively long time to obtain a result of the measurement. It may also be impossible to select particular regions of a sample to be measured. Due to the aforementioned drawbacks, the electron microscope has a limit in its practical use in the production line.

To address the aforementioned drawbacks, the technology using an optical measurement method has been developed and includes, for example, a method of using an approximate expression called the Effective Medium Approximation (EMA). A calculation method using the EMA has the problem in that, since an approximation is obtained by only a volume ratio of constituent substances in a given period, regardless of a detailed shape of a structure, it never distinguishes the detailed shape of the structure. That is, since the shape of each pattern of a circuit with a periodic structure is not specifically distinguished and only the volume ratio of constituent substances in a given period is distinguished, the difference between the real structure and the measured structure is significant. Specifically, in the periodic structure, since the calculation method using the EMA cannot clarify the different periodic structures if their volume ratios are same, a new optical measurement method is really needed.

SUMMARY OF THE INVENTION

Therefore, in an embodiment of the present invention, a nondestructive testing method is provided which is capable of analyzing a specific shape of a periodic structure and its internal components.

In a particular embodiment of the present invention, a nondestructive testing method is provided which is capable of precisely measuring a real shape of a periodic structure, considering a surface layer, such as an oxide layer or a coating layer formed on the periodic structure.

In accordance with one or more embodiments of the present invention, light from a light source is allowed to be incident on a real periodic structure, so that reflectivity or transmittance of the incident light or the physical properties related to the reflectivity and transmittance are measured. Further, in such embodiment, a virtual periodic structure can be set, and when light is incident on the virtual periodic structure, reflectivity or transmittance of the incident light or the physical properties related to the reflectivity and transmittance can be calculated and can be compared with the measured physical properties.

The virtual periodic structure may have periodicity in one dimension, two dimensions or three dimensions. For calculation, the virtual periodic structure may be horizontally divided into a plurality of layers. In middle layers of the divided virtual periodic structure, three substances may appear repeatedly in a given period.

The reflectivity, transmittance and the relevant physical properties of the virtual periodic structure may be calculated by using refractive indices of the substances forming the virtual periodic structure. The actually-measured reflectivity, transmittance and the relevant physical properties can be compared with the calculated corresponding physical properties and it can be determined whether the formation of the real periodic structure is identical with that of the virtual periodic structure.

The reflectivity or transmittance of the virtual periodic structure or both the reflectivity and the transmittance can be obtained, for example, from the Fourier series solutions for Maxwell's equations subject to the so-called Floquet conditions In accordance with one embodiment of the present invention, the virtual periodic structure can be divided into a zeroth order structure and a perturbed periodic structure which varies geometrically or physically relative to the zeroth order structure in a perturbation region. The physical properties related to the reflectivity and transmittance of the light incident on the zeroth order structure can be calculated such as by matching Fourier series solutions of Maxwell's equations in all divided layers, for example. Then, physical properties related to the reflectivity or transmittance of the perturbed virtual periodic structure or both can be obtained by solving a relevant Lippmann-Schwinger equation (See, e.g., Eq. 9 below), with Green's function (See, e.g., Eq. 8_below) of the zeroth order structure.

Accordingly, in accordance with one or more embodiments of the present invention, the formation and internal components of the periodic structure can be non-destructively tested.

In accordance with a particular embodiment of the present invention, microscopic change relative to an original periodic structure having a native oxide layer thereon or intentionally formed surface coating layer thereon can be precisely tested. The development of the semiconductor industry or other nano technology can benefit from such embodiment of the invention.

BRIEF DESCRIPTION OF THE DRAWINGS

Features and advantages of embodiments of the present invention will be apparent in accordance with the detailed description of preferred embodiments thereof with reference to the attached drawings in which.

DETAILED DESCRIPTION OF EMBODIMENTS OF THE INVENTION

Particular embodiments of the present invention will now be described more fully hereinafter with reference to the accompanying drawings.

Figure 1:
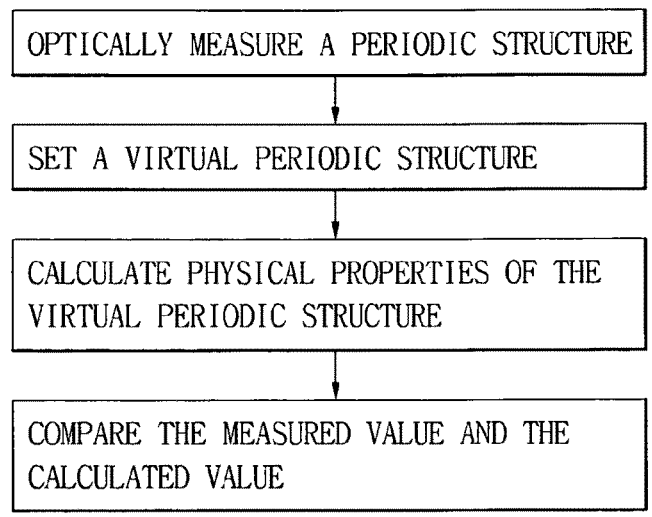
FIG. 1 is a flow chart schematically illustrating a testing method according to an embodiment of the present invention.

FIG. 1 is a flow chart schematically illustrating a testing method according to an embodiment of the present invention. By the testing method illustrated in FIG. 1, the formation and internal component of a periodic structure can be non-destructively tested. Specifically, shape, dimensions or both shape and dimensions of the periodic structure can be precisely determined, even when the periodic structure includes a native oxide layer formed on the periodic structure or an intentionally formed surface coating layer.

Measurement of Periodic Structure

Figure 2:
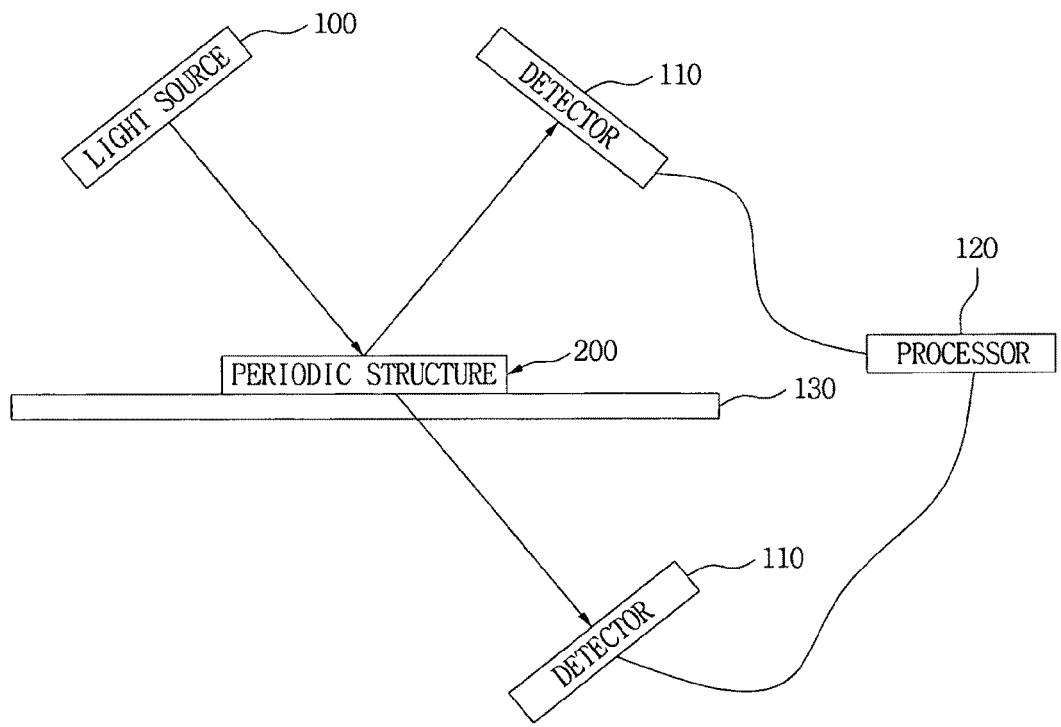
FIGS. 2 and 3 are block diagrams schematically illustrating testing devices of a periodic structure.
Figure 3:
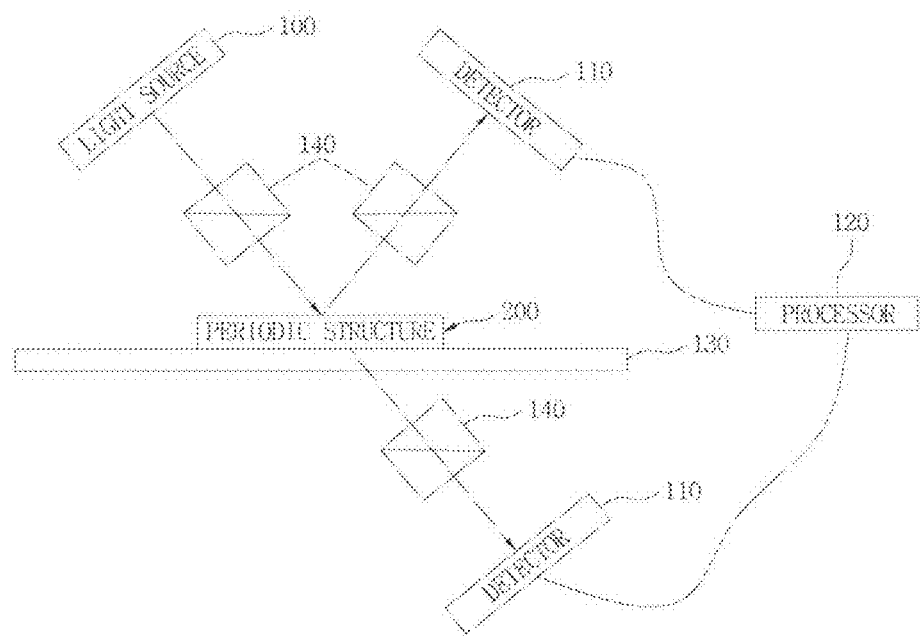

FIGS. 2 and 3 are block diagrams schematically illustrating testing devices for a periodic structure 200. Referring to FIG. 2, the testing devices comprise a light source 100, a detector 110 and a processor 120. When a periodic structure as a test object is positioned on a substrate 130, the light source 100 irradiates light having a specific wavelength or various wavelengths to the periodic structure 200. The light incident on the periodic structure 200 is partially transmitted and partially reflected. The reflected light is detected in the detector 110, and the reflectivity of a reflected wave measured in the detector 110 is calculated in the processor 120. The transmitted light is also detected in the detector 110, and the transmittance of a transmitted wave measured in the detector 110 is calculated in the processor 120.

The testing device may further comprise a polarizer 140 as illustrated in FIG. 3. In this case, the light generated from the light source 100 is polarized as the light of a TE mode or TM mode through the polarizer 140, to be incident on the periodic structure 200.

When the light is incident on the periodic structure 200, the incident light is divided into the reflected light and the transmitted light. In an embodiment of the present invention, reflectivity and transmittance in the most basic two polarization states in the reflection and transmission of the light, that is, the TE mode and the TM mode, are calculated to perform the nondestructive test of the periodic structure.

For example, the physical properties related to the reflectivity and transmittance which are measured by allowing the light to be incident on the periodic structure may be understood as the combination of the physical properties, which are related to an amplitude or phase of a reflected wave and a transmitted wave to an incident wave of a TE mode electric field, and the physical properties, which are related to an amplitude or phase of a reflected wave and a transmitted wave to an incident wave of a TM mode magnetic field.

Virtual Periodic Structure

Figure 4:
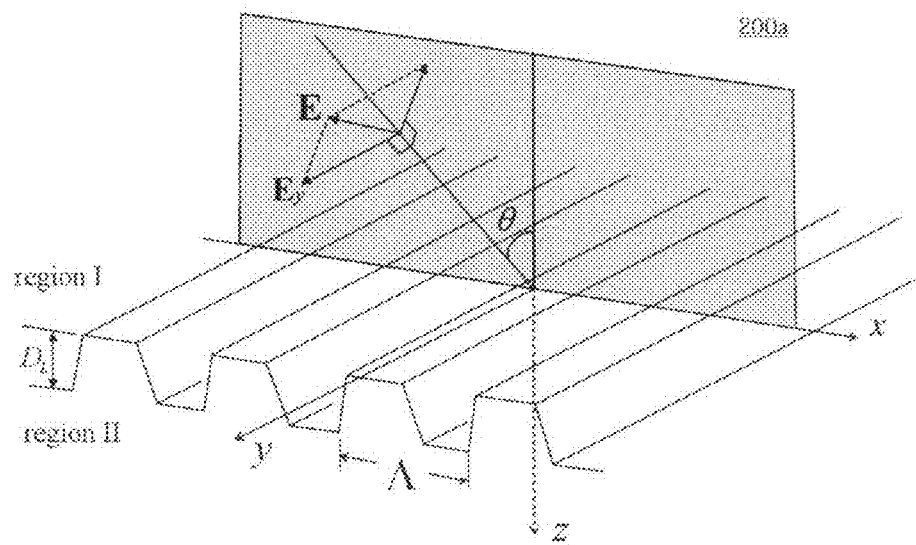
FIG. 4 is a perspective view illustrating an example of a virtual periodic structure.
Figure 5:
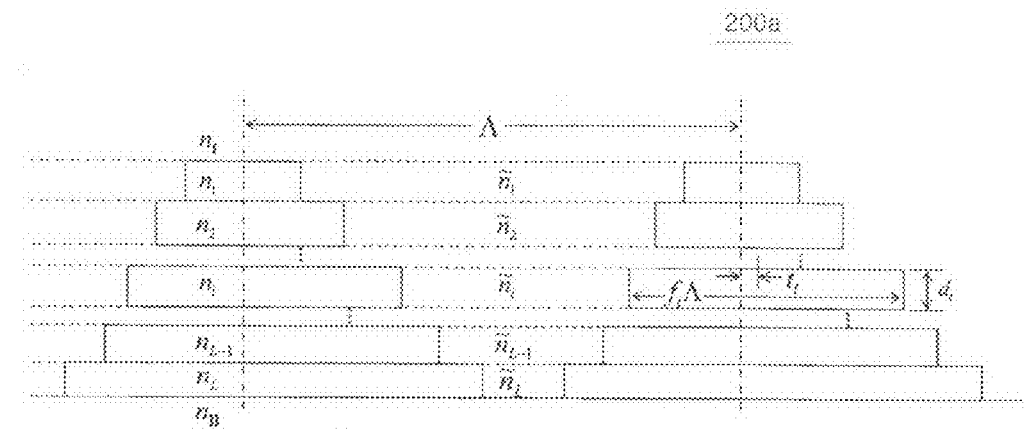
FIG. 5 is a sectional view of the virtual periodic structure of FIG. 4 being divided into a plurality of layers.

FIG. 4 is a perspective view illustrating the geometrical formation of a virtual periodic structure 200a, and FIG. 5 illustrates that a section of the virtual periodic structure 200a of FIG. 4 is divided into a plurality of layers.

In a case where the virtual periodic structure 200a is a semiconductor device having a shape of, for example, one-dimensional, two-dimensional or three-dimensional periodic formation, the virtual periodic structure 200a has the formation in which two substances of substance parts (from $n_1$ to $n_L$) formed of a substance, such as silicon and the like, in each layer and substance parts (from $\tilde{n}_1$ to $\tilde{n}_1$) of an incident part, such as an air layer and the like, are horizontally periodic.

However, in the real environments of the semiconductor process and the like, since it is impossible to fabricate the periodic structure in a perfect vacuum state, an oxide layer is formed on the surface of the real periodic structure by contact with air or water. Further, in the processing steps, since an intentional coating layer is formed on the surface of the periodic structure or a roughness layer is present on the surface of the periodic structure, the periodic structure of FIG. 4 has a limit in presuming the real geometrical shape thereof.

Figure 6:
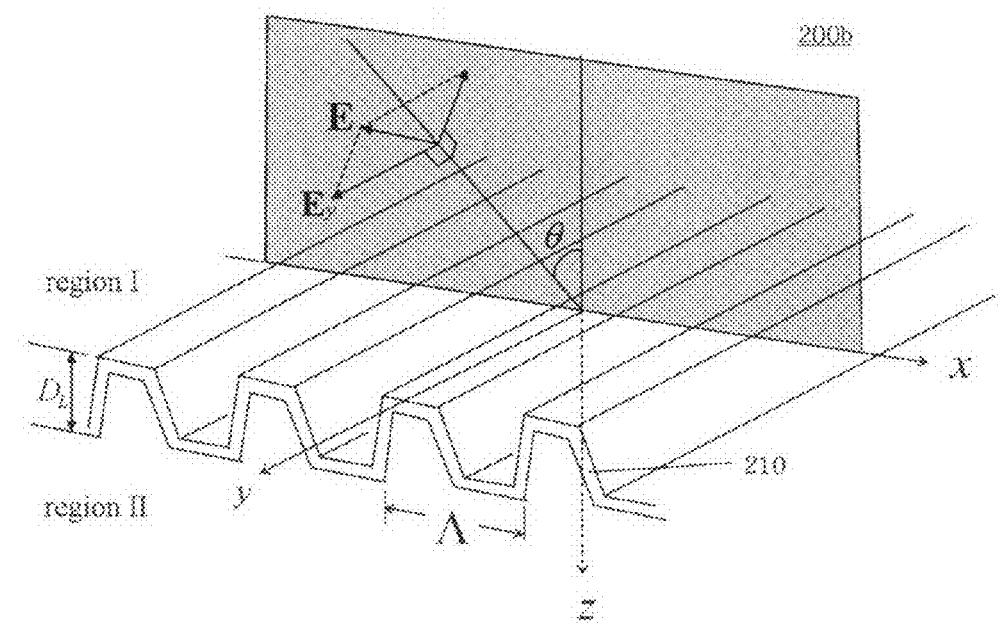
FIG. 6 is a perspective view of the geometrical formation of a virtual periodic structure according to an embodiment of the present invention.
Figure 7:
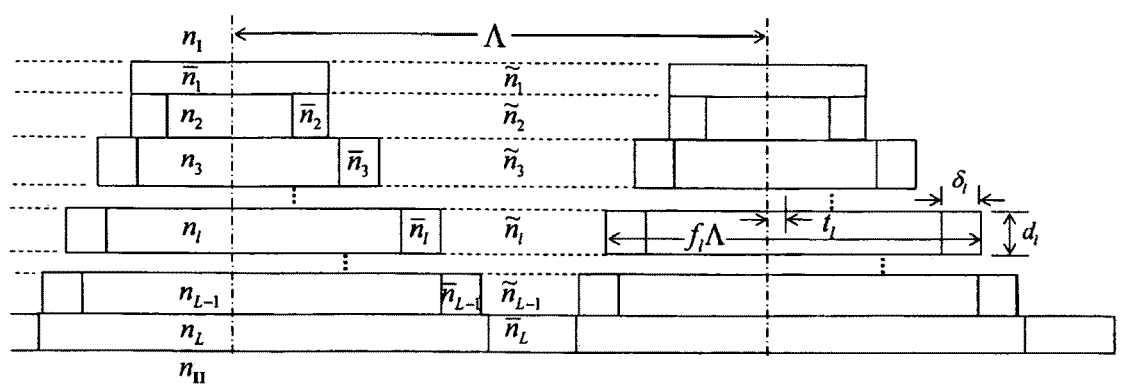
FIG. 7 is a sectional view of the virtual periodic structure of FIG. 6 being divided into a plurality of layers.

FIG. 6 illustrates the geometrical aspects, e.g., shape of a virtual periodic structure 200b according to an embodiment of the present invention. On the surface of the virtual periodic structure 200b, a surface layer 210, such as an oxide layer and the like, is formed. When a section of the virtual periodic structure 200b is divided into a plurality of layers, the virtual periodic structure 200b has the formation in which at least three substances are periodically repeated, as illustrated in FIG. 7. The virtual periodic structure 200b includes a ridge region formed at both sides of a third substance corresponding to a groove region. This ridge region is formed of a first substance forming a center part, and a second substance. The second substance includes the surface layer formed on the outer surface of the center part. In FIG. 7, $n_l$ (l=2, ..., L), $\tilde{n}_l$ (l=1, ..., L−1), and $\bar{n}_l$ (l=1, ..., L) are respectively representative of the ridge region (the first substance), the groove region (the third substance) and the surface layer region (the second substance). The ridge region may be formed of a single substance or two or more different substances being vertically or horizontally positioned. Accordingly, the first substance of the ridge region may be formed of a plurality of substances.

The surface layer region (the second substance) may be the oxide layer or the coating layer, or it may be the roughness layer of the periodic structure surface as the case may be. A third substance occupying the groove region may be in gaseous, liquid or solid state or a combination thereof.

For example, when the virtual periodic structure 200b is a semiconductor device, the plurality of layers (1 to L) except for the highest layer (layer 1) can be formed of the first substance being a semiconductor such as silicon and the like and the highest layer (layer 1) being a the second substance such as an oxide layer or a coating layer. A third substance being an air layer or other gas, liquid or solid state substance can be disposed in grooves between the layers 1 to L. The layers 1 to L and the third substance can be horizontally and periodically repeated within the periodic structure.

When the virtual periodic structure 200b is set by considering the surface layer 210, such as the oxide layer, coating layer or roughness layer of the surface, the reflectivity and transmittance of the virtual periodic structure is calculated to more closely approximate those of the real periodic structure. Consequently, the shape and components of the real periodic structure can be accurately measured. Specifically, it is possible to compare and analyze the geometrical shape and the internal component of the periodic structure, including the thicknesses of thin film structures present within the periodic structure.

Calculation of Physical Properties of Virtual Periodic Structure

The reflectivity and transmittance of light by a virtual periodic structure can be calculated by expanding refractive indices in Fourier series, and electric and magnetic fields in Floquet series. To account for vertical variation of the refractive index in the vertical direction, the direction aligned with the z axis (FIG. 4), the virtual periodic structure 200b is divided into the plurality of layers (1 to L) illustrated in FIG. 7, the refractive of index of each layer is assumed to be constant over the vertical height of the layer. More precise solutions can be obtained by increasing the number of the layers divided from the virtual periodic structure 200b and the number of terms of the Fourier series expansion.

The complex expansion coefficients of electric and magnetic waves in region I and region II gives the amplitude and phase of the reflected and transmitted waves, respectively. The expansion coefficients of dielectric function in each layer can be expressed in terms of complex refractive index of each of the first and second substances forming the ridge region and the third substance forming the groove region, a ratio $f_l$ of the region occupied by the first and second substances to a period $\Lambda$, a ratio $2\delta_1/\Lambda$ of the region occupied only by the second substance, and a parameter $t_l$ indicating how far the center of the layer l is from the center of layer 1 in the x direction, which will be described layer.

Further, in an embodiment of the present invention, to calculate the physical properties of the virtual periodic structure, a shape of the virtual periodic structure is assumed as a zeroth order periodic structure. Then, a perturbed periodic structure is obtained by applying a geometrical or physical change to the zeroth order periodic structure in a perturbation region.

To obtain the reflectivity or transmittance of the perturbed periodic structure, the Lippmann-Schwinger equation (Eq. 9 below) is solved numerically using the numerically calculated Green's function, reflectivity, and transmittance of the zeroth order structure as input values.

As described above, the reflectivity and transmittance of the zeroth order periodic structure can be calculated by solving Maxwell's Eqs. with Floquet's condition. For this purpose, the virtual periodic structure 200b is divided into the plurality of layers (1 to L) in the rectangular sectional shape, and subsequently, the dielectric function in each layer is expanded in Fourier series. When light is incident on the virtual periodic structure 200b, the reflected and transmitted waves in each layer are also expanded in Floquet series with coefficients to be determined by matching conditions of the electric and magnetic fields.

From the expansion coefficients thus determined, the reflectivity ($\rho_{TE}^{[0]}$ and $\rho_{TM}^{[0]}$) and the transmittance ($\tau_{TE}^{[0]}$ and $\tau_{[0]}^{TM}$) of the zeroth order periodic structure are calculated.

The Green's function of the zeroth order structure in the perturbation region can be obtained by applying the method of calculating the transmittance or reflectivity of the zeroth order periodic structure.

The reflectivity ($\rho_{TE}$ and $\rho_{TM}$) and the transmittance ($\tau_{TE}$ and $\tau_{TM}$) of the perturbed periodic structure can be calculated from the expansion coefficients of a coupled wave of the TE mode electric field and the TM mode magnetic field in each layer of perturbed structure obtained by solving the Lippmann-Schwinger equation.

In accordance with an embodiment of the present invention, the periodic structure between an incident medium (region I) and a substrate (region II) is divided into L layers, including some of or the whole of layers being formed of a uniform substance. The divided grating structures are classified into the following cases: the case where each layer in all layers of the whole perturbation region is formed of a uniform substance (case 1); (ii) the case where all layers of the perturbation region are formed of a single uniform substance (case 2); (iii) the case where the perturbation region is placed as the air layer on the substrate (case 3); and (iv) the case where each layer is not formed of a uniform substance but all layers are formed of one given layer being repeated (case 4).

In accordance with an embodiment of the present invention, there are provided the results of specific calculation of each case 1, case 2, case 3 and case 4, specifically, considering the periodic structure with the surface layer, which will be described later.

Comparison of the Measured Value with the Calculated Value

The actually-measured reflectivity or transmittance of the periodic structure are compared with the calculated reflectivity or transmittance of the virtual periodic structure. Alternatively, the actually-measured reflectivity or transmittance of the periodic structure are compared with the calculated reflectivity or transmittance of the virtual periodic structure. In another alternative, properties related to the actual reflectivity or transmittance of the periodic structure are compared with properties related to the calculated reflectivity or transmittance of the virtual periodic structure. When these values are the same within a given error range, the real periodic structure, as determined from measurements of reflectivity or transmittance, can be determined as being identical with that of the virtual periodic structure 200b determined by calculating values of reflectivity or transmittance.

When comparing the measured reflectivity and transmittance with the calculated reflectivity and transmittance, an additional device, such as, for example, a computer may be used for comparing the measured value with the calculated value. By this method, geometry, e.g., shape and dimensional aspects of the real periodic structure 200 can be precisely and efficiently determined.

In the measurement experiment of the periodic structure, diverse physical properties related to reflectivity ρ and transmittance τ are measured. The relevant presumed value related to the measured physical properties can be obtained by the reflectivity ρ and transmittance τ being calculated based on the mathematical methods.

EMBODIMENT

Figure 8:
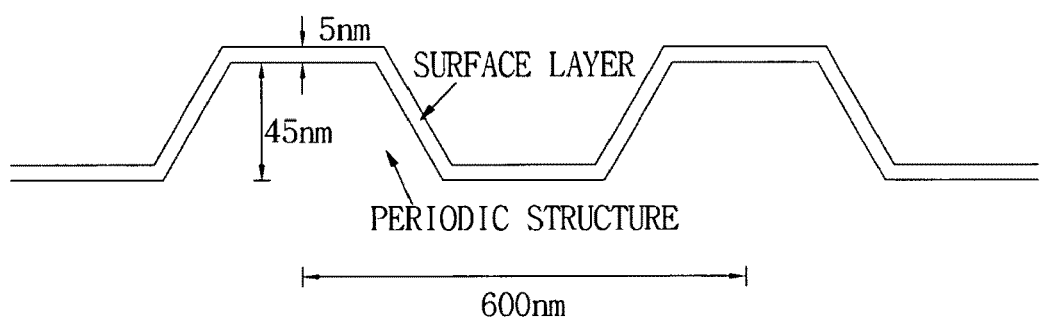
FIG. 8 is a sectional view of the geometrical formation of a virtual periodic structure according to an embodiment of the present invention.

As an embodiment of the present invention, a virtual periodic structure where a surface layer is formed is set as illustrated in FIG. 8. This virtual periodic structure has a repeated period of 60 nm. The thickness of a ridge region formed of silicon crystals is 45 nm, an oxide is formed on the surface of the ridge region to the thickness of 5 nm, and the slope of a ridge is set as 81°.

The slope and period of the virtual periodic structure and the width and height of the ridge may be varied as random values. Further, the geometrical shape thereof may have a random shape.

The physical properties of the virtual periodic structure are calculated by using the method according to an embodiment of the present invention, to be compared with the measured values of a real periodic structure.

Figure 9:
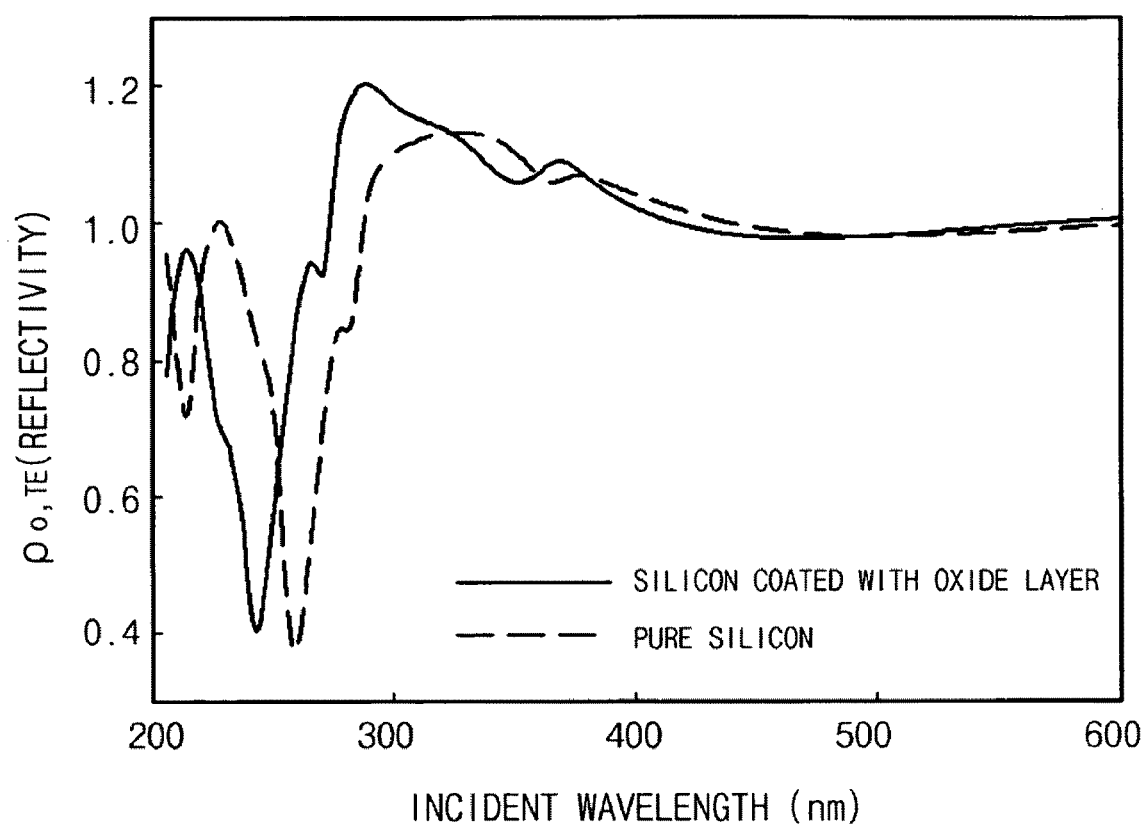
FIGS. 9 and 10 are graphs respectively illustrating results of calculating the reflectivity of a virtual periodic structure considering an oxide layer and calculating the reflectivity of a virtual periodic structure not considering the oxide layer in a TE mode and a TM mode.
Figure 10:
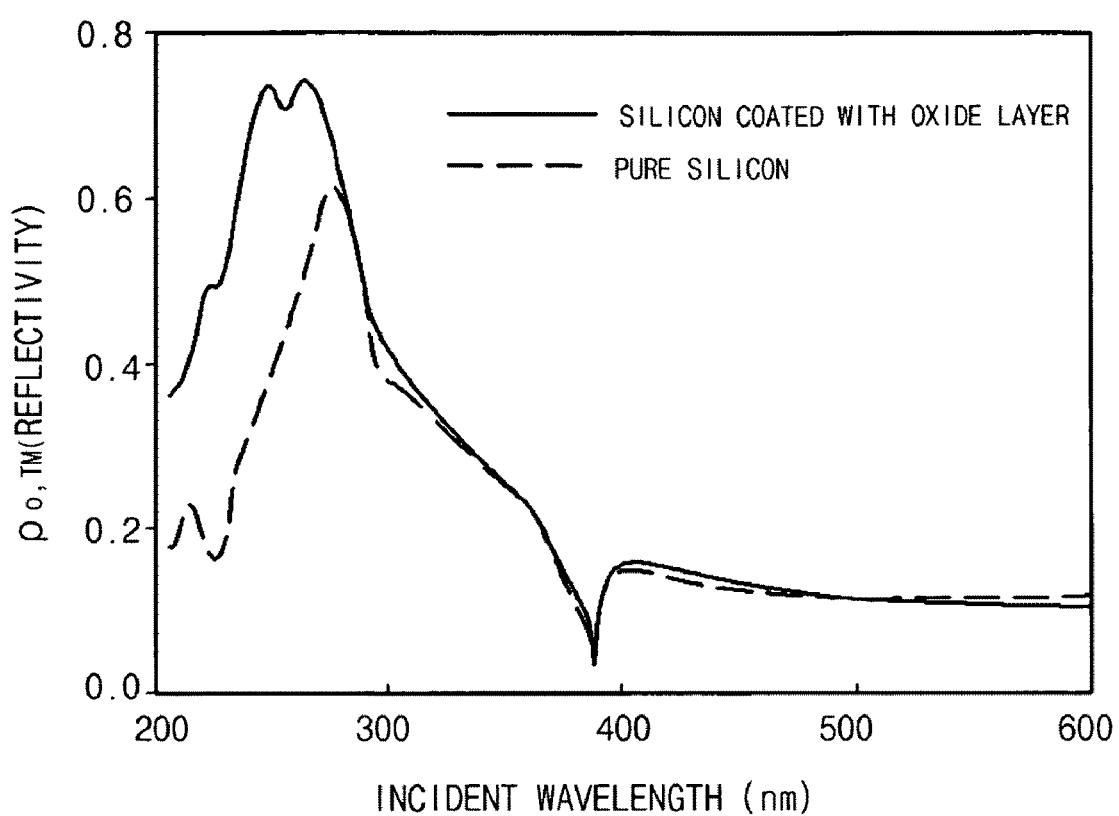

FIGS. 9 and 10 are graphs respectively illustrating results of the calculated reflectivity of the virtual periodic structure considering the oxide layer as illustrated in FIG. 8 and the calculated reflectivity of the virtual periodic structure not considering the oxide layer in a TE mode and a TM mode. That is, the reflectivity of an incident wavelength in each of the TE mode and the TM mode is calculated, assuming a case where the oxide layer is considered, i.e., the virtual periodic structure is formed of silicon coated with the oxide layer, and another case where the oxide layer is not considered, i.e., the virtual periodic structure is formed of pure silicon.

Based on the results as illustrated, the calculated value of the reflectivity of the pure silicon is considerably different from that of the reflectivity of the silicon coated with the oxide layer. That is, the extent of approximation of the virtual periodic structure to the real periodic structure significantly varies, depending on whether or not we assume the presence of the surface layer, such as the oxide layer and the like. In the case of measuring the formation of the real periodic structure in which the surface layer, such as the oxide layer and the like, is formed, if the virtual periodic structure is assumed to be formed of the pure silicon only, the calculated values of the virtual periodic structure are never identical with the measured values of the real periodic structure. When the real periodic structure to be measured includes the surface layer, such as the oxide layer and the like, the extent of identity with the real periodic structure obviously increases only when the virtual periodic structure is assumed to be formed of silicon coated with the oxide layer.

Figure 11:
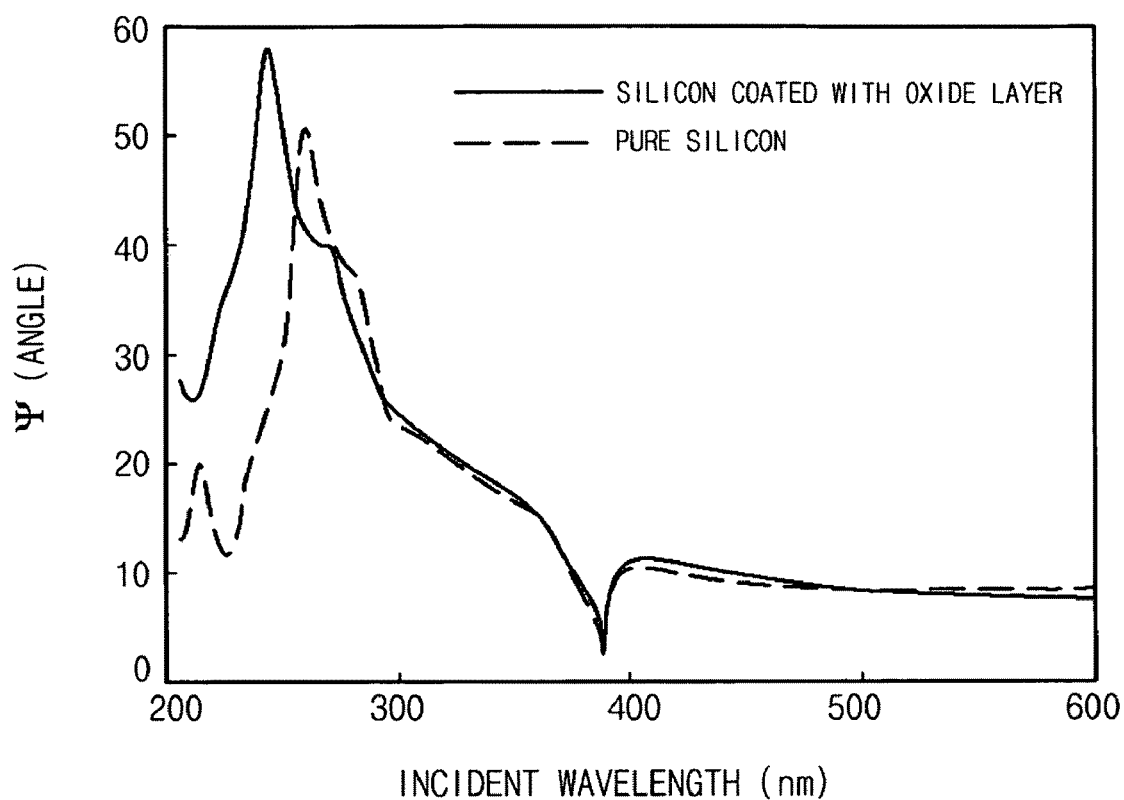
FIGS. 11 and 12 are graphs illustrating results of extracting the physical properties measured by ellipsometry from the calculation results of FIGS. 9 and 10.
Figure 12:
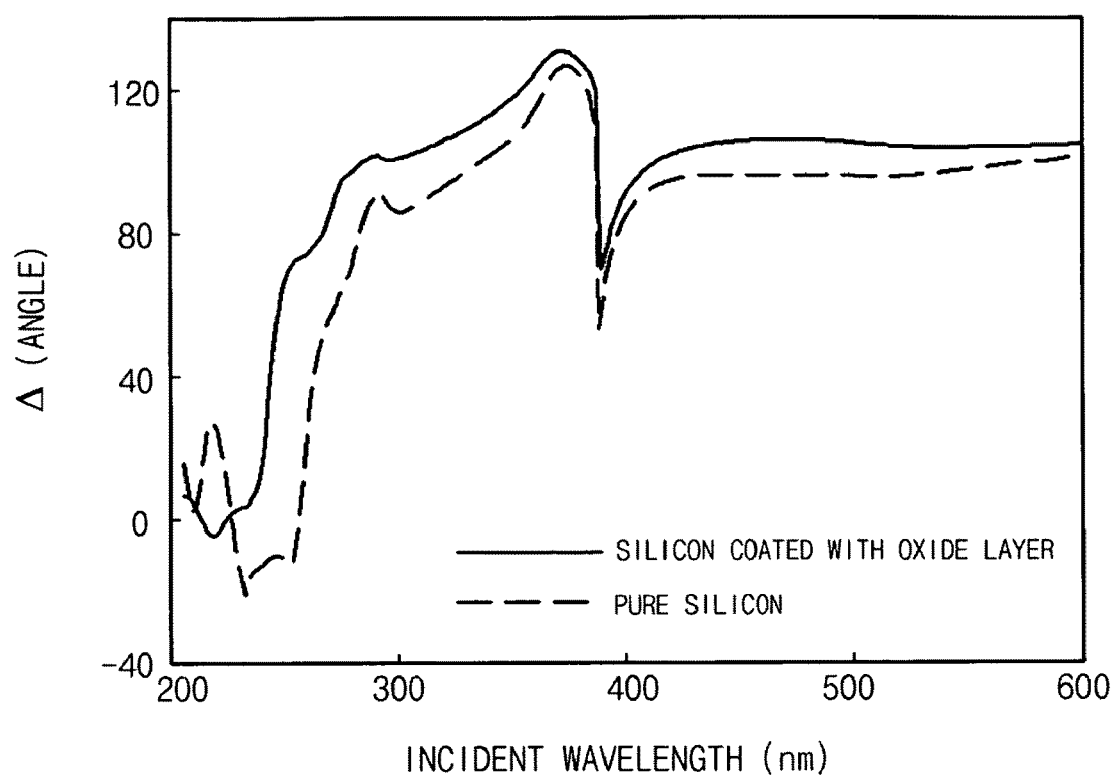

FIGS. 11 and 12 are graphs illustrating results of the extracted physical properties measured by ellipsometry from the calculation results of FIGS. 9 and 10. The graphs show that diverse physical properties can be obtained from the results of calculation using the method in accordance with an embodiment of the present invention. Specifically, the graphs illustrate the results of the calculated amplitude and phase of the reflectivity ratio between the TM mode $\rho_M$ and the TE mode $\rho_E$ as the physical properties $\Psi$ and $\Delta$ measured by general ellipsometry. The analysis results of the graphs show that there is a big difference between the virtual periodic structure formed of the pure silicon and the virtual periodic structure formed of the silicon coated with the oxide layer. As described above, upon comparing with the formation of the real periodic structure by extracting the diverse physical properties from the reflectivity or transmittance, if the formation of the virtual periodic structure is assumed considering the presence of the oxide layer, the more accurate formation of the real periodic structure is presumed.

The method of calculating the reflectivity and transmittance of the virtual periodic structure 200b illustrated in FIGS. 6 and 7 according to other embodiments of the present invention will be described below:

I. Lippmann-Schwinger Equation: TE Mode

Due to the periodicity of the periodic structure in x direction, the TE mode solutions to Maxwell's equation can be written as $$E_y(x, z) = \sum_{n=-\infty}^{\infty} S_{yn}(z) e^{ik_{xn}x} \quad \text{Eq. (1)}$$

$$H_x(x, z) = i\left(\frac{\epsilon_0}{\mu_0}\right)^{1/2} \sum_{n=-\infty}^{\infty} U_{xn}(z) e^{ik_{xn}x} \quad \text{Eq. (2)}$$

where $\vec{i} = \sqrt{-1}$; $k_{xn} = k_0[n_I \sin\theta - n(\lambda_0/\Lambda)]$; $k_0 = 2\pi/\lambda_0$ (with $\lambda_0$ being the wavelength of an incident wave in vacuum, $n_I$ being the refractive index of an incident region, and θ being the incident angle); $\epsilon_0$ is the permittivity of the vacuum, and $\mu_0$ is the permeability of the vacuum.

The dielectric function of the periodic structure with a one-dimensional period being equal to Λ in x direction can be expanded in Fourier series:

$$\varepsilon(x, z) = \sum_{h=-\infty}^{\infty} \varepsilon_h(z) e^{i2\pi hx/\Lambda} \quad \text{Eq. (3)}$$

From Maxwell's equations, $S_{yn}(z)$ in Eq. (1) and $U_{xn}(z)$ in Eq. (2) are combined as follows:

$$\begin{bmatrix} (1/k_0)\partial S_y(z)/\partial z \\ (1/k_0)\partial U_x(z)/\partial z \end{bmatrix} = \begin{bmatrix} 0 & I \\ A(z) & 0 \end{bmatrix} \begin{bmatrix} S_y(z) \\ U_x(z) \end{bmatrix} \quad \text{Eq. (4)}$$

where I is a unit matrix of dimension 2N+1 and $$A(z) \equiv K_x^2 - E(z) \quad \text{Eq. (5)}$$

where $K_x$ is a diagonal matrix with the (n,n) element being equal to $k_{xn}/k_0$ and E(z) is a matrix formed by the permittivity harmonic components, with the (n,p) element being equal to $E_{np}(z) = \epsilon_{(n-p)}(z)$.

Below, coupled-wave-basis indices are truncated so that they run from –N to N.

Combining two first order differential equations in Eq. (4), we obtain $$\left[\frac{1}{k_0^2}\frac{\partial^2}{\partial z^2} - A(z)\right]S_y(z) = 0 \qquad \text{Eq. (6)}$$

With the superscript [0], indicating the zeroth order structure, we obtain a similar Eq.:

$$\left[\frac{1}{k_0^2}\frac{\partial^2}{\partial z^2} - A^{[0]}(z)\right]S_y^{[0]}(z) = 0 \qquad \text{Eq. (7)}$$

A corresponding Green's function can be formulated as follows:

$$\left[\frac{1}{k_0^2}\frac{\partial^2}{\partial z^2} - A^{[0]}(z)\right]G(z, z') = -\delta(z-z')I \qquad \text{Eq. (8)}$$

From Eqs. (6), (7) and (8) are, we obtain the Lippman-Schwinger equation:

$$S_y(z) - S_y^{[0]}(z) = \int dz' G(z,z') Y(z') S_y(z') \qquad \text{Eq. (9)}$$

where $Y(z) \equiv E(z) - E(z) - E^{[0]}(z)$. In Eq. (9), since $Y(z)=0$ outside the perturbation zone, the integration region is restricted within the perturbation region.

II. Calculation of $S_y^{[0]}(z)$

In this section, we omit the superscript [0] used in the previous section to indicate the relevant quantities in the zeroth order periodic structure.

A. Division of Periodic Structure Region into Layers

We approximate the periodic structure, which includes an oxide layer, a coating layer or a surface layer, to a stack of parallel rectangular layers with a common period $\Lambda$, whereby the z dependency of the dielectric function $\epsilon(x,z)$ is shifted to the index l indicating the layer. Then, the dielectric function of the given layer l is indicated as $\epsilon^{(l)}(x)$ and can be expressed as follows:

$$\epsilon^{(l)}(x) = \sum_h \epsilon_h^{(l)} e^{i2\pi hx/\Lambda} \qquad \text{Eq. (10)}$$

The expansion coefficient $\epsilon_h^{(l)}$ in Eq. (10) is given in each layer as follows:

$l = 1$ $$\epsilon_0^{(1)} = \bar{n}_1^2 f_1 + \tilde{n}_1^2(1-f_1) \qquad \text{Eq. (11)}$$

$$\epsilon_h^{(1)} = (\bar{n}_1^2 - \tilde{n}_1^2)\frac{\sin(\pi h f_1)}{\pi h} \text{ from } l=2 \text{ to } L-1 \qquad \text{Eq. (12)}$$

$$\epsilon_0^{(l)} = \left[(n_l^2 - \bar{n}_l^2)f_l + (\bar{n}_l^2 - \tilde{n}_l^2)\frac{2\delta_l}{\Lambda} + \tilde{n}_l^2\right]e^{-i2\pi t_l/\Lambda} \qquad \text{Eq. (13)}$$

$$\epsilon_h^{(l)} = \frac{1}{\pi h}\left[(\bar{n}_l^2 - \tilde{n}_l^2)\sin(\pi h f_l) + (n_l^2 - \bar{n}_l^2)\sin\left(\pi h f_l - \frac{2\pi h\delta_l}{\Lambda}\right)\right]e^{-i2\pi t_l/\Lambda} \qquad \text{Eq. (14)}$$

-continued $$\epsilon_0^{(l)} = \left[n_L^2\left(f_{L-1} - \frac{2\delta_{L-1}}{\Lambda}\right) + \bar{n}_L^2\left(1 - f_{L-1} + \frac{2\delta_{L-1}}{\Lambda}\right)\right]e^{-i2\pi t_{L-1}/\Lambda} \qquad \text{Eq. (15)}$$

$$\epsilon_h^{(l)} = \frac{1}{\pi h}(n_L^2 - \bar{n}_L^2)\sin\left[\pi h\left(f_{L-1} - \frac{2\delta_{L-1}}{\Lambda}\right)\right]e^{-i2\pi t_{L-1}/\Lambda} \qquad \text{Eq. (16)}$$

where $\eta_l$ (l=2, ..., L), $\tilde{\eta}_l$ (l=1, ..., L-1), and $\bar{\eta}_l$ (l=1, ..., L) are respectively complex refractive index of the ridge region, groove region and surface layer region in the layer l, $f_l$ is the fraction of the period $\Lambda$ occupied by the ridge region (the first and second substances), $2\delta_l/\Lambda$ is the fraction of the period occupied by the oxide layer region (the second substance) only, and $t_l$ ($t_1=t_2=0$) is the center-shifting parameter of the layer l relative to the center of layer 1 in x direction.

In the division of the periodic structure into layers, some of or whole of the layers may be formed of a uniform substance. As described above, the multilayer Ga structure indicates the case where each layer in all layers is formed of a uniform substance, and the single layer Ga structure indicates the case where all layers are formed of a single uniform substance. Further, when each layer is not formed of a uniform substance but all layers are formed of one given layer which is repeated, it is defined as a single layer G1 structure. Specifically, region II of FIG. 6 may be an air layer.

The solutions of the electric field and magnetic field in regions I and II can be represented by using Floquet's conditions as follows:

$$E_y^{(0)}(x, z) = \sum_{n=-N}^{N} S_{yn}^{(0)}(z) e^{ik_{xn}x} \qquad \text{Eq. (17)}$$

$$H_x^{(0)}(x, z) = i\left(\frac{\epsilon_0}{\mu_0}\right)^{1/2} \sum_{n=-N}^{N} U_{xn}^{(0)}(z) e^{ik_{xn}x} \qquad \text{Eq. (18)}$$

$$E_y^{(L+1)}(x, z) = \sum_{n=-N}^{N} S_{yn}^{(L+1)}(z) e^{ik_{xn}x} \qquad \text{Eq. (19)}$$

$$H_x^{(L+1)}(x, z) = i\left(\frac{\epsilon_0}{\mu_0}\right)^{1/2} \sum_{n=-N}^{N} U_{xn}^{(L+1)}(z) e^{ik_{xn}x} \qquad \text{Eq. (20)}$$

$$S_{yn}^{(0)}(z) = \delta_{0n} e^{ik_{L,zn}z} + \rho_n e^{-ik_{L,zn}z} \qquad \text{Eq. (21)}$$

$$U_{xn}^{(0)}(z) = \delta_{0n}(ik_{L,zn}/k_0) e^{ik_{L,zn}z} - \rho_n(ik_{L,zn}/k_0) e^{-ik_{L,zn}z} \qquad \text{Eq. (22)}$$

$$S_{yn}^{(L+1)}(z) = \tau_n e^{ik_{II,zn}(z-Z_L)} \qquad \text{Eq. (23)}$$

$$U_{xn}^{(L+1)}(z) = \tau_n(ik_{II,zn}/k_0) e^{ik_{II,zn}z} \qquad \text{Eq. (24)}$$

$$k_{\ell,zn} = \begin{cases} k_0[n_\ell^2 - (k_{xn}/k_0)^2]^{1/2} & \text{for } k_0 n_\ell > k_{xn} \\ ik_0[(k_{xn}/k_0)^2 - n_\ell^2]^{1/2} & \text{for } k_{xn} > k_0 n_\ell; \ell = I, II \end{cases} \qquad \text{Eq. (25)}$$

where $n_I$ and $n_{II}$ are the complex refractive index of the incident medium and the substrate. The first term on the right-hand side of Eq. (21) represents the incident wave.

The electric field and the magnetic field in the periodic structure regions (l=1, ..., L) can be expanded in terms of coupled-wave bases:

$$E_y^{(l)}(x,z) = \sum_{n=-N}^{N} S_{yn}^{(l)}(z)e^{ik_{xn}x} \quad \text{Eq. (26)}$$

$$H_x^{(l)}(x,z) = i\left(\frac{\epsilon_0}{\mu_0}\right)^{1/2} \sum_{n=-N}^{N} U_{xn}^{(l)}(z)e^{ik_{xn}x} \quad \text{Eq. (27)}$$

When Eq. (7) is applied to the layer l, we obtain an Eq. for $S_{yn}^{(l)}$ (n=−N, . . . , N) in Eq. (26) as follows:

$$(1/k_0^2)\partial^2 S_y^{(l)}(z)/\partial z^2 = A_l S_y^{(l)}(z) \quad \text{Eq. (28)}$$

where $$A_l \equiv K_x^2 - E_l \quad \text{Eq. (29)}$$

where the (n,p) element of $E_l$ is equal to $E_{l,np} = \epsilon_{(n-p)}^{(l)}$.

Solutions $S_y^{(l)}(z)$ and $U_x^{(l)}(z)$ to Eq. (28) are given as follows:

$$S_y^{(l)}(z) = W_l[e^{-k_0 Q_l(z-z_{l-1})} f_l + e^{k_0 Q_l(z-z_{l-1})} g_l] \quad \text{Eq. (30)}$$

$$U_x^{(l)}(z) = V_l[-e^{-k_0 Q_l(z-z_{l-1})} f_l + e^{k_0 Q_l(z-z_{l-1})} g_l] \quad \text{Eq. (31)}$$

where $W_l$ is a square matrix constructed from (2N+1) eigenvectors of $A_l$, $Q_l$ is a diagonal matrix with the element being the positive square root of (2N+1) eigenvalue of $A_l$, and $V_l = W_l Q_l$; $f_l$ and $g_l$ are column vectors to be determined from boundary conditions; $z_l-1$ is the z coordinate of the interface between the layer l−1 and the layer l.

Eqs. (21), (22), (23) and (24), respectively, can be written in the following matrix form:

$$S_y^{(0)}(z) = W_0[e^{-k_0 Q_0 z} f_0 + e^{k_0 Q_0 z} g_0], \quad \text{Eq. (32)}$$

$$U_x^{(0)}(z) = V_0[-e^{-k_0 Q_0 z} f_0 + e^{k_0 Q_0 z} g_0], \quad \text{Eq. (33)}$$

$$S_y^{(L+1)}(z) = W_{L+1}[e^{-k_0 Q_{L+1}(z-z_L)} f_{L+1} + e^{k_0 Q_{L+1}(z-z_L)} g_{L+1}], \quad \text{Eq. (34)}$$

$$U_x^{(L+1)}(z) = V_{L+1}[-e^{-k_0 Q_{L+1}(z-z_L)} f_{L+1} + e^{k_0 Q_{L+1}(z-z_L)} g_{L+1}], \quad \text{Eq. (35)}$$

where $Q_0$ and $Q_{L+1}$ are diagonal matrices with the n-th diagonal elements being $-ik_{I,zn}/k_0$ and $-ik_{II,zn}/k_0$, respectively; all of $f_0 = (0, \ldots, 0, 1, 0, \ldots, 0)^T$, $g_0 = (\rho_{-N}, \ldots \rho_{-1}, \rho_0, \rho_1, \ldots \rho_N)^T$, $f_{L+1} = (\tau_{-N}, \ldots, \tau_{-1}, \tau_0, \tau_1, \ldots, \tau_N)^T$, $g_{L+1} = (0, \ldots, 0)^T$ are (2N+1)-component column vectors; $W_0 = I$, $V_0 = W_0 Q_0$, $W_{L+1} = I$ and $V_{l+1} = W_{L+1} Q_{L+1}$.

are

B. Calculation of $f_l$ and $g_l$

By applying the boundary conditions which the electric field and the magnetic field satisfy at $z=z_l$ (l=0, . . . , L), we have $$\begin{bmatrix} f_l \\ g_l \end{bmatrix} = \begin{bmatrix} X_l^{-1} & 0 \\ 0 & X_l \end{bmatrix} \begin{bmatrix} M_l^+ & M_l^- \\ M_l^- & M_l^+ \end{bmatrix} \begin{bmatrix} f_{l+1} \\ g_{l+1} \end{bmatrix}, \text{ where} \quad \text{Eq. (36)}$$

$$X_l \equiv \begin{cases} e^{-k_0 Q_l d_l} & \text{for } l=1, \ldots, L \\ I & \text{for } l=0 \end{cases}, \quad \text{Eq. (37)}$$

$$M_l^\pm \equiv \frac{1}{2}[W_l^{-1} W_{l+1} \pm V_l^{-1} V_{l+1}] \quad \text{Eq. (38)}$$

Because $A_l$ is symmetric matrix, eigenvectors of $A_l$ are orthogonal. Thus, when the normalized-eigenvector matrix $W_l$ is used, $W_l^T$ for $W_l^{-1}$ may be used to enhance the efficiency of numerical calculation.

The recursion relation of Eq. (36) will eventually yield the following form:

$$\begin{bmatrix} f_l \\ g_l \end{bmatrix} = \begin{bmatrix} a_l \\ b_l \end{bmatrix} f_{L+1} \quad \text{Eq. (39)}$$

Eliminating $f_{L+1}$ from Eq. (39), we obtain:

$$g_l = b_l a_l^{-1} f_l = R_l f_l \quad \text{Eq. (40)}$$

Substituting these $g_l$ and $g_{l+1} = R_l f_{l+1}$ into Eq. (36), we obtain the recursion relation for $R_l$ (l=0, 1, . . . , L):

$$R_l = X_l(M_l^- + M_l^+ R_{l+1})(M_l^+ + M_l^- R_{l+1})^{-1} X_l. \quad \text{Eq. (41)}$$

By applying this recursion relation repeatedly starting from l=L with the initial setting value $R_{L+1} = 0$ obtain all values of $R_l$.

Now that we have an algorithm to determine $R_l$ (l=0, . . . , L) in Eq. (40), the remaining problem in determining $S^{(l)}$'s completely is to calculate $f_l$'s. Since $f_0$ is known, $f_l$ can be calculated by applying the transfer matrix method from the incident medium to layer l.

To this end, the recursion relation of Eq. (36) is inverted to obtain $$f_{l+1} = (N_l^+ X_l + N_l^- X_l R_l) f_l \text{ where} \quad \text{Eq. (42)}$$

$$N_l^\pm = \frac{1}{2}[W_{l+1}^{-1} W_l \pm V_{l+1}^{-1} V_l] \quad \text{Eq. (43)}$$

By repeated applications of Eq. (42) with the initial setting $f_0 = (0, \ldots, 0, 1, 0, \ldots, 0)^T$, all $f_l$'s are determined.

III. Calculation of G(z,z'): TE Mode

If z locates inside the layer l, Eq. (8) becomes:

$$\left[\frac{1}{k_0^2}\frac{\partial^2}{\partial z^2} - A_l\right] G(z, z') = -\delta(z - z')I \quad \text{Eq. (44)}$$

In this section, we omit, as in section II, the superscript [0] used to indicate the relevant quantities in the zeroth order periodic structure. For the given layer l, $A_l$ is not a function of z any more. The solutions to Eq. (44) are of the following forms:

$$G_{ll'}(z,z') = \begin{cases} W_l[e^{-k_0 Q_l(z-z_{l-1})} f_{ll'}^-(z') + \\ \quad e^{k_0 Q_l(z-z_{l-1})} g_{ll'}^-(z')] \\ \quad (\text{for } l < l') \\ W_l[e^{-k_0 Q_l(z-z_{l-1})} f_{ll'}^-(z') + \\ \quad e^{k_0 Q_l(z-z_{l-1})} g_{ll'}^-(z')] \\ \quad (\text{for } l = l'; z < z') \\ W_l[e^{-k_0 Q_l(z-z_{l-1})} f_{ll'}^+(z') + \\ \quad e^{k_0 Q_l(z-z_{l-1})} g_{ll'}^+(z')] \\ \quad (\text{for } l = l'; z > z') \\ W_l[e^{-k_0 Q_l(z-z_{l-1})} f_{ll'}^+(z') + \\ \quad e^{k_0 Q_l(z-z_{l-1})} g_{ll'}^+(z')] \\ \quad (\text{for } l > l') \end{cases} \quad \text{Eq. (45)}$$

where $W_l$ and $Q_L$ are square matrices constructed from eigenvectors and eigenvalues of $A_l$ as in section II; and $f_{ll'}^\pm(z')$ and $g_{ll'}^\pm(z')$, which are constant (in z) square matrices to be determined by matching the boundary conditions; and the paired subscripts ll' in $G_{ll'}(z,z')$, $f_{ll'}^\pm(z')$, and $g_{ll'}^\pm(z')$, are to denote that a field point z locates inside the layer l and a source point z' locates inside the layer l'. When an index l=0 is assigned to region I and an index l=L+1 is assigned to region II, the solutions in these regions can be written as follows:

$$G_{ll'(z,z')} \begin{cases} W_0[e^{-k_0 Q_0 z} f_{0l'}^-(z') + \\ e^{k_0 Q_0 z} g_{0l'}^-(z')] \\ \text{(for } l = 0 < l') \\ W_{L+1}[e^{-k_0 Q_{L+1}(z-z_L)} f_{L+1,l'}^+(z') + \\ e^{k_0 Q_{L+1}(z-z_L)} g_{L+1,l'}^+(z')] \\ \text{(for } l = L+1 > l') \end{cases} \quad \text{Eq. (46)}$$

where $W_0$, $Q_0$, $W_{L+1}$, $Q_{L+1}$ are the same as defined previously, and $f_{0l'}^-(z')$ and $g_{L+1,l'}^+(z')$ are zero matrices.

A. Application of Transfer Matrix Method from Substrate (l=L+1) to Source Layer (l=l')

Applying matching conditions for $G(z,z')$ and $G'(z, z') \equiv \partial G(z,z')/\partial z$ at $z=z_l$ (l=l', ..., L), we obtain a recursion relation of the similar form to Eq. (36):

$$\begin{bmatrix} f_{ll'}^+(z') \\ g_{ll'}^+(z') \end{bmatrix} = \begin{bmatrix} X_l^{-1} & 0 \\ 0 & X_l \end{bmatrix} \begin{bmatrix} M_l^+ & M_l^- \\ M_l^- & M_l^+ \end{bmatrix} \begin{bmatrix} f_{l+1,l'}^+(z') \\ g_{l+1,l'}^+(z') \end{bmatrix} \quad \text{Eq. (47)}$$

where $X_l$ and $M_l^\pm$ are as defined in Eqs. (37) and (38). Repeated applications of Eq. (47) will eventually yield:

$$\begin{bmatrix} f_{ll'}^+(z') \\ g_{ll'}^+(z') \end{bmatrix} = \begin{bmatrix} a_l^+ \\ b_l^+ \end{bmatrix} f_{L+1,l'}^+(z') \quad \text{Eq. (48)}$$

Eliminating $f_{L+1,l'}^+(z')$, we obtain $$g_{ll'}^+(z') = b_l^+(a_l^+)^{-1} f_{ll'}^+(z') \equiv R_l f_{ll'}^+(z') \quad \text{Eq. (49)}$$

Substituting Eq. (49) into Eq. (47), we obtain the same recursion relation as in Eq. (41)

$$R_l = X_l(M_l^- + M_l^+ R_{l+1})(M_l^+ + M_l^- R_{l+1})^{-1} X_l \quad \text{Eq. (50)}$$

Because the initial setting value $R_{L+1}=0$ is the same, we can use $R_l$ determined in section II, without repeating the same calculation.

Since we have Eq. (49) relating $g_{ll'}^+(z')$ and $f_{ll'}^+(z')$ and Eq. (50) giving the algorithm to determine $R_l$, $f_{ll'}^+(z')$ should be solved to obtain $G_{ll'}(z,z')$. As a first step, we will express $f_{ll'}^+(z')$ in terms of $f_{l'l'}^+(z')$. To this end, Eq. (47) is inverted to have $$\begin{bmatrix} f_{l+1,l'}^+(z') \\ g_{l+1,l'}^+(z') \end{bmatrix} = \begin{bmatrix} N_l^+ & N_l^- \\ N_l^- & N_l^+ \end{bmatrix} \begin{bmatrix} X_l & 0 \\ 0 & X_l^{-1} \end{bmatrix} \begin{bmatrix} f_{ll'}^+(z') \\ g_{ll'}^+(z') \end{bmatrix} \quad \text{Eq. (51)}$$

which, together with Eq. (49), gives a recursion relation for $f_{ll'}^+(z')$:

$$f_{l+1,l'}^+(z') = (N_l^+ X_l + N_l^- X_l R_l) f_{ll'}^+(z') \quad \text{Eq. (52)}$$

$$\equiv \Psi_l f_{ll'}^+(z')$$

Applying Eq. (52) repeatedly, for l=l'+1, ..., L, we obtain $$f_{ll'}^+(z') = \Psi_{l-1} \ldots \Psi_{l'} f_{l'l'}^+(z') \quad \text{Eq. (53)}$$

Once $f_{l'l'}^+(z')$ is obtained, all of $f_{ll'}^+(z')$ and $g_{ll'}^+(z')$ are determined. Before obtaining $f_{l'l'}^+(z')$, we return to the problem of obtaining $G_{ll'}(z,z')$ for l<l'.

B. Application of Transfer Matrix Method from Incident Medium (l=0) to Source Layer (l=l')

Matching conditions for $G(z,z')$ and $G'(z,z') \equiv \partial G(z,z')/\partial z$ at $z=z_l$ (l=0, ..., l'−1) yield $$\begin{bmatrix} f_{l+1,l'}^-(z') \\ g_{l+1,l'}^-(z') \end{bmatrix} = \begin{bmatrix} N_l^+ & N_l^- \\ N_l^- & N_l^+ \end{bmatrix} \begin{bmatrix} X_l & 0 \\ 0 & X_l^{-1} \end{bmatrix} \begin{bmatrix} f_{ll'}^-(z') \\ g_{ll'}^-(z') \end{bmatrix} \quad \text{Eq. (54)}$$

where $X_l$ and $N_l^\pm$ are as defined previously. Using Eq. (54) repeatedly, we obtain $$\begin{bmatrix} f_{ll'}^-(z') \\ g_{ll'}^-(z') \end{bmatrix} = \begin{bmatrix} a_l^- \\ b_l^- \end{bmatrix} g_{0l'}^-(z') \quad \text{Eq. (55)}$$

By elimination of $g_{0l'}^-(z')$ in this equation, $f_{ll'}^-(z')$ can be expressed in terms of $g_{ll'}^-(z')$:

$$f_{ll'}^-(z') = a_l^-(b_l^-)^{-1} g_{ll'}^-(z') \equiv \bar{r}_l g_{ll'}^-(z') \quad \text{Eq. (56)}$$

Eliminating $f_{l+1,l'}^-(z')$ and $f_{ll'}^-(z')$ in Eq. (54) by using Eq. (56), we obtain a recursion relation:

$$\bar{r}_{l+1} = (N_l^- + N_l^+ X_l \bar{r}_l X_l)(N_l^+ + N_l^- X_l^{-1} \bar{r}_l X_l)^{-1} \quad \text{Eq. (57)}$$

By repeated applications of this recursion relation starting from l=0 with the initial setting $\bar{r}_0=0$, we obtain all values of $\bar{r}_l$.

Since $f_{ll'}^-(z')$ is expressed in terms of $g_{ll'}^-(z')$, the remaining problem is to determine $g_{ll'}^-(z')$. To this end, $g_{ll'}^-(z')$ is expressed in terms of $g_{l'l'}^-(z')$. By application of the boundary conditions at $z=z_l$ (l<l'), a matching equation of the form given in Eq. (47) is obtained $$\begin{bmatrix} f_{ll'}^-(z') \\ g_{ll'}^-(z') \end{bmatrix} = \begin{bmatrix} X_l^{-1} & 0 \\ 0 & X_l \end{bmatrix} \begin{bmatrix} M_l^+ & M_l^- \\ M_l^- & M_l^+ \end{bmatrix} \begin{bmatrix} f_{l+1,l'}^-(z') \\ g_{l+1,l'}^-(z') \end{bmatrix} \quad \text{Eq. (58)}$$

From Eq. (58) and Eq. (56), we obtain a recursion relation for $g_{ll'}^-(z')$:

$$g_{ll'}^-(z') = X_l(M_l^- \bar{r}_{l+1} + M_l^+) g_{l+1,l'}^-(z') \quad \text{Eq. (59)}$$

$$\equiv \Phi_{l+1} g_{l+1,l'}^-(z')$$

which enables us to express $g_{ll'}^-(z')$ (l=1, ..., l'−1) in terms of $g_{l'l'}^-(z')$:

$$g_{ll'}^-(z') = \Phi_{l+1} \ldots \Psi_{l'} g_{l'l'}^-(z') \quad \text{Eq. (60)}$$

When $g_{l'l'}^-(z')$ is obtained, all values of $g_{ll'}^-(z')$ and $f_{ll'}^-(z')$ (l=1, ..., l'−1) are determined.

C. Application of Boundary Conditions of G and ∂G/∂z at z=z'

Now let us fix $f_{l'l'}^{+}(z')$ and $g_{l'l'}^{-}$. Since $G_{l'l'}(z,z')$ is continuous and $\partial G_{l'l'}(z, z')/\partial z$ is the discontinuous at $z=z'$ by a delta function on the right-hand side in Eq. (44), we obtain $$\begin{bmatrix} f_{l'l'}^{+}(z') \\ g_{l'l'}^{-}(z') \end{bmatrix} = \frac{k_0}{2} \begin{bmatrix} [I - \bar{r}_{l'}R_{l'}]^{-1} & -\bar{r}_{l'}[I - R_{l'}\bar{r}_{l'}]^{-1} \\ R_{l'}[I - \bar{r}_{l'}R_{l'}]^{-1} & -[I - R_{l'}\bar{r}_{l'}]^{-1} \end{bmatrix}$$
$$\begin{bmatrix} e^{k_0 Q_{l'}(z'-z_{l'-1})} \\ -e^{-k_0 Q_{l'}(z'-z_{l'-1})} \end{bmatrix} Q_{l'}^{-1} W_{l'}^T \qquad \text{Eq. (61)}$$

With $u_{l'} = (I - R_{l'}\bar{r}_{l'})^{-1}$, Eq. (61) can be written as $$f_{l'l'}^{+}(z') = \frac{k_0}{2}\left[e^{k_0 Q_{l'}(z'-z_{l'-1})} + \bar{r}_{l'}u_{l'}\left[R_{l'}e^{k_0 Q_{l'}(z'-z_{l'-1})} + e^{-k_0 Q_{l'}(z'-z_{l'-1})}\right]\right]Q_{l'}^{-1}W_{l'}^T \qquad \text{Eq. (62)}$$

$$g_{l'l'}^{-}(z') = \frac{k_0}{2}u_{l'}\left[R_{l'}e^{k_0 Q_{l'}(z'-z_{l'-1})} + e^{-k_0 Q_{l'}(z'-z_{l'-1})}\right]Q_{l'}^{-1}W_{l'}^T \qquad \text{Eq. (63)}$$

From Eqs. (62), (63), (53) and (60), the Green's function of Eq. (45) is completely determined.

IV. Numerical Implementation: TE Mode

A. Discretization of Lippmann-Schwinger Equation

Two quantities, $S_y^{[0]}(z)$ and $G(z,z')$, which are defined by the physical properties and geometrical formation of the zeroth order periodic structure and the information of the incident wave, and the perturbation potential $Y(z)$ are input parameters. An unknown quantity $S_y(z)$ to be determined by the physical properties and geometrical formation of the perturbed periodic structure and the information of the same incident wave is to be obtained by solving the Lippmann-Schwinger equation iteratively.

It is assumed that the perturbation function $Y(z')$ has a constant value $Y_j$ inside layer j. By setting $z \rightarrow z_{l-1}$ for z locating inside the layer l (l=1, ..., L) and $z \rightarrow z_L$ for z locating inside the layer L and by using Eqs. (53) and (60), we transform Eq. (9) as follows:

$$S_y(z_{l-1}) - S_y^{[0]}(z_{l-1}) = \qquad \text{Eq. (64)}$$

$$W_l\Bigg[(1+R_l)\sum_{j=1}^{l-1}\Psi_{l-1}\ldots\Psi_j\int_{z_{j-1}}^{z_j} dz' f_{jj}^{+}(z')Y_j S_y(z') +$$

$$(\bar{r}_l+1)\int_{z_{l-1}}^{z_l} dz' g_{ll}^{-}(z')Y_l S_y(z') +$$

$$(\bar{r}_l+1)\sum_{j=l+1}^{L}\Phi_{l+1}\ldots\Phi_j\int_{z_{j-1}}^{z_j} dz' g_{jj}^{-}(z')Y_j S_y(z')\Bigg]$$

$$S_y(z_L) - S_y^{[0]}(z_L) = W_L(X_L + X_L^{-1}R_L) \qquad \text{Eq. (65)}$$

$$\Bigg[\sum_{j=1}^{L-1}\Psi_{L-1}\ldots\Psi_j\int_{z_{j-1}}^{z_j} dz' f_{jj}^{+}(z')Y_j S_y(z') +$$

$$\int_{z_{L-1}}^{z_L} dz' f_{LL}^{+}(z')Y_L S_y(z')\Bigg]$$

It is noted that, in Eq. (64), if l=1, $$\sum_{j=1}^{l-1}(\ldots)$$

generates no terms and if l=L, $$\sum_{j=l+1}^{L}(\ldots)$$

generates no terms.

To enhance accuracy, we carry out analytic integrations within each segment by using the interpolation formula $$S_y(z') = S_y(z_{j-1}) + \qquad \text{Eq. (66)}$$
$$S_y'(z_j)(z' - z_{j-1})(z_{j-1} < z' < z_j; j = 1, \ldots, L) \text{ where}$$

$$S_y'(z_j) \equiv [S_y(z_j) - S_y(z_{j-1})]/d_j, \, d_j \equiv z_j - z_{j-1} \qquad \text{Eq. (67)}$$

Eq. (64) becomes, for l = 2, ..., L−1, $$S_y(z_{l-1}) - S_y^{[0]}(z_{l-1}) = \qquad \text{Eq. (68)}$$

$$\sum_{j=0}^{l-2}\Theta_{l-1,j}^{(+)}Y_{j+1}S_y(z_j) + \sum_{j=l-1}^{L-1}\Theta_{l-1,j}^{(-)}Y_{j+1}S_y(z_j) +$$

$$\sum_{j=1}^{l-1}\overline{\Theta}_{l-1,j}^{(+)}Y_j S_y(z_j) + \sum_{j=1}^{L}\overline{\Theta}_{l-1,j}^{(-)}Y_j S_y(z_j), \text{ for } l = 1,$$

$$S_y(z_0) - S_y^{[0]}(z_0) = \sum_{j=0}^{L-1}\Theta_{0,j}^{(-)}Y_{j+1}S_y(z_j) + \sum_{j=1}^{L}\overline{\Theta}_{0,j}^{(-)}Y_j S_y(z_j), \qquad \text{Eq. (69)}$$

for l = L, $$S_y(z_{L-1}) - S_y^{[0]}(z_{L-1}) = \qquad \text{Eq. (70)}$$

$$\sum_{j=0}^{L-2}\Theta_{L-1,j}^{(+)}Y_{j+1}S_y(z_j) + \Theta_{L-1,L-1}^{(-)}Y_L S_y(z_{L-1}) +$$

$$\sum_{j=1}^{L-1}\overline{\Theta}_{L-1,j}^{(+)}Y_j S_y(z_j) + \overline{\Theta}_{L-1,L}^{(-)}Y_L S_y(z_L)$$

Eq. (65) becomes $$S_y(z_L) - S_y^{[0]}(z_L) = \sum_{j=0}^{L-1}\Theta_{L,j}^{(+)}Y_{j+1}S_y(z_j) + \sum_{j=1}^{L}\overline{\Theta}_{L,j}^{(+)}Y_j S_y(z_j) \qquad \text{Eq. (71)}$$

Eqs. (68), (69), (70) and (71) can be put together in one expanded matrix form of a linear system of equations:

$$\mathbf{S} - \mathbf{S}^{[0]} = [\mathbf{G}\mathbf{Y} + \overline{\mathbf{G}}\,\overline{\mathbf{Y}}]\mathbf{S} \qquad \text{Eq. (72)}$$

where $\mathbf{S}$ and $\mathbf{S}^{[0]}$ are column vectors of dimension L+1 with the layer components $S_y(z_l)$ and $S_y^{[0]}(z_l)$ respectively. Each layer component $S_y(z_l)$ and $S_y^{[0]}(z_l)$ are still column vectors of dimension (2N+1) with the coupled-wave basis components.

$\mathbf{G}$, $\overline{\mathbf{G}}$, $\mathbf{Y}$, $\overline{\mathbf{Y}}$ are square matrices with $(L+1)^2$ layer components, each layer component being $(2N+1)^2$ square matrices in coupled-wave:

$$\mathbf{G}_{lm} = \begin{cases} \Theta_{lm}^{(+)} & \text{for } l > m, m \neq L \\ \Theta_{lm}^{(-)} & \text{for } l \leq m, m \neq L \\ 0 & \text{for } m = L \end{cases} \qquad \text{Eq. (73)}$$

-continued $$\mathbb{G}_{lm} = \begin{cases} 0 & \text{for } l = 0 \\ \Theta_{lm}^{(+)} & \text{for } l \neq 0, l \geq m \\ \Theta_{lm}^{(-)} & \text{for } l \neq 0, l < m \end{cases} \quad \text{Eq. (74)}$$

$$\mathbb{Y}_{lm} = \begin{cases} Y_{l+1}\delta_{lm} & \text{for } l \neq L \\ 0 & \text{for } l = L \end{cases} \quad \text{Eq. (75)}$$

$$\bar{\mathbb{Y}}_{lm} = \begin{cases} 0 & \text{for } l = 0 \\ Y_l \delta_{lm} & \text{for } l \neq 0 \end{cases} \quad \text{Eq. (76)}$$

B. Special Cases

As special cases, (i) If each layer is a homogeneous medium (case 1), we obtain $$W_1 = \ldots = W_L = I \quad \text{Eq. (77)}$$

whereby $R_l$, $\bar{r}_l$, $u_l$, $\Psi_l$, $\Phi_l$ become diagonal matrixes. As a result, since matrix elements $\mathbb{G}_{lm}$ and $\bar{\mathbb{G}}_{lm}$ in Eqs. (73) and (74) all become diagonal matrixes, we obtain more simplified formulas.

(ii) If a zeroth order dielectric function of each layer is the same (case 4), that is, when $\epsilon^{[0]}(1)(x,z) = \ldots = \epsilon^{[0](L)}(x,z)$, we obtain $$W_1 = \ldots = W_L = W \quad \text{Eq. (78)}$$

$$Q_1 = \ldots = Q_L = Q \quad \text{Eq. (79)}$$

whereby simplified matrix elements $\mathbb{G}_{lm}$ and $\bar{\mathbb{G}}_{lm}$ $\bar{\mathbb{G}}_{lm}$ can be obtained.

(iii) Furthermore, if each layer is homogeneous (case 2), $$W_1 = \ldots = W_L = I \quad \text{Eq. (80)}$$

$$Q_1 = \ldots = Q_L = qI \quad \text{Eq. (81)}$$

whereby more simply expressed matrix elements can be obtained.

(iv) If the perturbation region is taken as the incident medium (case 3), this corresponds to case 2 with u=O. Thus, the matrix elements become much simpler.

C. Calculation of $S_y(z)$

To enhance the speed of calculation of multiplying a matrix and a vector in the space of the coupled-wave basis, the perturbation matrix can be block-diagonalized from a similarity transformation with $$T = \frac{1}{2} \begin{bmatrix} -I_N & 0_c & J_N \\ 0_r & I_1 & 0_r \\ J_N & 0_c & I_N \end{bmatrix} \quad \text{Eq. (82)}$$

where $I_K$ is a K×K unit matrix, $J_N$ is an N×N square matrix with elements $J_{ij} = \delta_{i,N+1-j}$, and $O_c$ and $O_r$ are, respectively, zero column and zero row vectors of dimension N.

To solve the matrix equation of Eq. (72) iteratively, we start with an initial settings $\mathbb{S} = \mathbb{S}^{[0]}$. We substitute this into Eq. (72), $$\mathbb{S}^{[0]} = \mathbb{S}^{[0]} {}_{-}[\mathbb{G}\mathbb{Y}_+ \bar{\mathbb{G}}\bar{\mathbb{Y}}]\mathbb{S}^{[0]} \quad \text{Eq. (83)}$$

If both sides of this resulting equation are not equal within a given error range, we substitute a new $\mathbb{S}$ defined as the right-hand side of Eq. (83), $$\mathbb{S} = \mathbb{S}^{[0]} {}_{-}[\mathbb{G}\mathbb{Y}_+ \bar{\mathbb{G}}\bar{\mathbb{Y}}]\mathbb{S}^{[0]} \quad \text{Eq. (84)}$$

into Eq. (72) to obtain $$\mathbb{S}^{[0]} {}_{-}[\mathbb{G}\mathbb{Y}_+ \bar{\mathbb{G}}\bar{\mathbb{Y}}]\mathbb{S}^{[0]} = \mathbb{S}^{[0]} {}_{-}[\mathbb{G}\mathbb{Y}_+ \bar{\mathbb{G}}\bar{\mathbb{Y}}](\mathbb{S}^{[0]} {}_{-} \mathbb{G}\mathbb{Y}_+ \bar{\mathbb{G}}\bar{\mathbb{Y}}]\mathbb{S}^{[0]}) \quad \text{Eq. (85)}$$

We compare both sides of this equation. If the comparison does not give a satisfactory result, we define a new $\mathbb{S}$ as the right-hand side of Eq. (85):

$$\mathbb{S} = \mathbb{S}^{[0]} {}_{-}[\mathbb{G}\mathbb{Y}_+ \bar{\mathbb{G}}\bar{\mathbb{Y}}](\mathbb{S}^{[0]} {}_{-} \mathbb{S}^{[0]} {}_{+} \bar{\mathbb{G}}\bar{\mathbb{Y}}]\mathbb{S}^{[0]}) \quad \text{Eq. (86)}$$

With this $\mathbb{S}$, we test the validity of Eq. (72). This process of comparison will be continued until a satisfactory result is obtained.

D. Calculation of $g_0$ and $f_{L+1}$

The final goal we wish to achieve is to calculate reflectivity $\rho_n$ and transmittance $\tau_n$ related to the order n of the coupled-wave basis. The reflectivity column vector $g_0 = (\rho_{-N}, \ldots, \rho_{-1}, \rho_0, \rho_1, \ldots, \rho_N)^T$ can be extracted as follows:

$$g_0 = g_0^{[0]} + \sum_{l=0}^{L} \sum_{m=0}^{L} [\mathbb{G}_{0l}\mathbb{Y}_{lm} + \bar{\mathbb{G}}_{0l}\bar{\mathbb{Y}}_{lm}]\mathbb{S}_m \quad \text{Eq. (87)}$$

$g_0^{[0]} = (\rho_{-N}^{[0]}, \ldots, \rho_{-1}^{[0]}, \rho_0^{[0]}, \rho_1^{[0]}, \ldots, \rho_N^{[0]})^T$ is the zeroth order reflectivity column vector. The middle component of Eq. (87), $\rho_0 = (g_0)_0$, characterizes a reflection due to the principal order.

Similarly, the transmittance column vector $f_{L+1} = (\tau_{-N}, \ldots, \tau_{-1}, \tau_0, \tau_1, \ldots, \tau_N)^T$ is given as follows:

$$f_{L+1} = f_{L+1}^{[0]} + \sum_{l=0}^{L} \sum_{m=0}^{L} [\mathbb{G}_{0l}\mathbb{Y}_{lm} + \bar{\mathbb{G}}_{0l}\bar{\mathbb{Y}}_{lm}]\mathbb{S}_m \quad \text{Eq. (88)}$$

where the components of zeroth order transmittance column vector are $f_{L+1}^{[0]} = (\tau_{-N}^{[0]}, \ldots, \tau_{-1}^{[0]}, \tau_0^{[0]}, \tau_1^{[0]}, \ldots, \tau_N^{[0]})^T$, and $\tau_0 = (f_{L+1})_0$ is the transmittance of a transmitted wave by the principal order.

V. Lippmann-Schwinger Equation: TM Mode

Due to the periodicity of the periodic structure in x direction, the TM mode solutions to Maxwell's Eqs. can be expressed as $$H_y(x,z) = \sum_{n=-\infty}^{\infty} U_{yn}(z) e^{ik_{xn}x} \quad \text{Eq. (89)}$$

$$E_x(x,z) = -i\left(\frac{\mu_0}{\epsilon_0}\right)^{1/2} \sum_{n=-\infty}^{\infty} S_{xn}(z) e^{ik_{xn}x} \quad \text{Eq. (90)}$$

The inverse of the dielectric function $\epsilon(x,z)$ can be expanded in Fourier series as follows:

$$\frac{1}{\varepsilon(x,z)} \sum_{h=-\infty}^{\infty} \varepsilon_h^{\#}(z) e^{i2\pi hx/\Lambda} \quad \text{Eq. (91)}$$

From Maxwell's equations, $U_{yn}(z)$ and $S_{xn}(z)$ are coupled via two linear differential equations. Eliminating $S_{xn}(z)$, one can get a second-order decoupled differential equation of $U_{yn}(z)$:

$$\left[\frac{1}{k_0^2}\frac{\partial^2}{\partial z^2} - \frac{1}{k_0^2}\frac{\partial E(z)}{\partial z}E^{-1}(z)\frac{\partial U_y(z)}{\partial z} - \right.$$
$$\left. E(z)B(z)\right]U_y(z) = 0 \text{ where}$$
Eq. (92)

$$B(z) = K_x P(z) K_x - I$$
Eq. (93)

where $P(z)$ is a square matrix with the $(n,p)$ element being equal to $P_{np}(z)=\epsilon_{(n-p)}^{\#}(z)$. A similar equation for the zeroth order periodic structure with the same period can be obtained by using the superscript [0]:

$$\left[\frac{1}{k_0^2}\frac{\partial^2}{\partial z^2} - \frac{1}{k_0^2}\frac{\partial E^{[0]}(z)}{\partial z}(E^{[0]})^{-1}(z)\frac{\partial U_y^{[0]}(z)}{\partial z} - \right.$$
$$\left. E^{[0]}(z)B^{[0]}(z)\right]U_y^{[0]}(z) = 0$$
Eq. (94)

Corresponding Green's function is given as follows:

$$\left[\frac{1}{k_0^2}\frac{\partial^2}{\partial z^2} - \frac{1}{k_0^2}\frac{\partial E^{[0]}(z)}{\partial z}(E^{[0]})^{-1}(z)\frac{\partial U_y^{[0]}(z)}{\partial z} - \right.$$
$$\left. E^{[0]}(z)B^{[0]}(z)\right]G(z,z') = -\delta(z-z')I$$
Eq. (95)

Based on the standard method, combining Eqs. (92), (94) and (95), we obtain the Lippmann-Schwinger equation for the TM mode as follows:

$$U_y(z) - U_y^{(0)}(z) = \int dz'\left[k_0^2 G(z')K_x\tilde{Y}(z')K_x U_y(z') + \frac{\partial G(z,z')}{\partial z'}Y(z')\frac{\partial U_y(z')}{\partial z'}\right] Y(z) \equiv E^{-1}(z) - (E^{[0]})^{-1}(z)$$
Eq. (96)

where

VI. Calculation of $U_y^{[0]}(z)$

In this section, we omit the superscript [0] used in the previous section to indicate the relevant quantities in the zeroth order periodic structure.

Solutions to the electric field and the magnetic field in region I and region II can be expanded in the coupled-wave basis by the Floquet's conditions:

$$H_y^{(0)}(x,z) = \sum_{n=-N}^{N} U_{yn}^{(0)}(z)e^{ik_{xn}x}$$
Eq. (97)

$$E_x^{(0)}(x,z) = -i\left(\frac{\mu_0}{\epsilon_0}\right)^{1/2}\sum_{n=-N}^{N} S_{xn}^{(0)}(z)e^{ik_{xn}x}$$
Eq. (98)

$$H_y^{(L+1)}(x,z) = \sum_{n=-N}^{N} U_{yn}^{(L+1)}(z)e^{ik_{xn}x}$$
Eq. (99)

$$E_x^{(L+1)}(x,z) = -i\left(\frac{\mu_0}{\epsilon_0}\right)^{1/2}\sum_{n=-N}^{N} S_{xn}^{(L+1)}(z)e^{ik_{xn}x} \text{ where}$$
Eq. (100)

-continued $$U_{yn}^{(0)}(z) = \delta_{n0}e^{ik_{1,zn}z} + \rho_n e^{-ik_{1,zn}z}$$
Eq. (101)

$$S_{xn}^{(0)}(z) = \delta_{n0}\left(\frac{ik_{1,zn}}{n_1^2 k_0}\right)e^{ik_{1,zn}z} - \rho_n\left(\frac{ik_{1,zn}}{n_1^2 k_0}\right)e^{-ik_{1,zn}z}$$
Eq. (102)

$$U_{yn}^{(L+1)}(z) = T_n e^{ik_{11,zn}(z-z_L)}$$
Eq. (103)

$$S_{xn}^{(L+1)}(z) = T_n\left(\frac{ik_{11,zn}}{n_{11}^2 k_0}\right)e^{ik_{11,zn}(z-z_L)}$$
Eq. (104)

The first term on the right-hand side of Eq. (101) represents the incident wave. Likewise, solutions of the electric field and the magnetic field in the periodic structure region (l=1, ..., L) can be expanded in terms of coupled-wave bases as follows:

$$H_y^{(l)}(x,z) = \sum_{n=-N}^{N} U_{yn}^{(l)}(z)e^{ik_{xn}x}$$
Eq. (105)

$$E_x^{(l)}(x,z) = -i\left(\frac{\mu_0}{\epsilon_0}\right)^{1/2}\sum_{n=-N}^{N} S_{xn}^{(l)}(z)e^{ik_{xn}x}$$
Eq. (106)

Applying Eq. (92) to the layer l, we obtain an equation for $U_{yn}^{(l)}$ (n=-N, ..., N) in Eq. (105):

$$(1/k_0^2)\partial^2 U_y^{(l)}/\partial z^2 = E_l B_l U_y^{(l)}$$
Eq. (107)

where $E_l$ is as defined in section II, and $B_l$, being independent of $z_l$ is defined as follows:

$$B_l = K_x E_l^{-1} K_x - I$$
Eq. (108)

Solutions to Eq. (107) are given as $$U_y^{(l)}(z) = W_l[e^{-k_0 Q_l(z-z_{l-1})}f_l + e^{k_0 Q_l(z-z_{l-1})}g_l]$$
Eq. (109)

$$S_x^{(l)}(z) = V_l[e^{-k_0 Q_l(z-z_{l-1})}f_l + e^{k_0 Q_l(z-z_{l-1})}g_l]$$
Eq. (110)

where $W_l$ is a square matrix constructed from (2N+1) eigenvectors of $E_l B_l$, $Q_l$ is a diagonal matrix with the diagonal elements being the positive square roots of (2N+1) eigenvalues of $E_l B_l$, $V_l = E_l^{-1} W_l Q_l$, and $f_l$ and $g_l$ are column vectors with (2N+1) components to be determined by application of the boundary conditions.

The components of the coupled-wave basis in Eqs. (101), (102), (103) and (104), respectively, can be expressed in the matrix form as follows:

$$U_y^{(0)}(z) = W_0[e^{-k_0 Q_0 z}f_0 + e^{k_0 Q_0 z}g_0]$$
Eq. (111)

$$S_x^{(0)}(z) = V_0[e^{-k_0 Q_0 z}f_0 + e^{k_0 Q_0 z}g_0]$$
Eq. (112)

$$U_y^{(L+1)}(z) = W_{L+1}[e^{-k_0 Q_{L+1}(z-z_L)}f_{L+1} + e^{k_0 Q_{L+1}(z-z_L)}g_{L+1}]$$
Eq. (113)

$$S_x^{(L+1)}(z) = V_{L+1}[e^{-k_0 Q_{L+1}(z-z_L)}f_{L+1} + e^{k_0 Q_{L+1}(z-z_L)}g_{L+1}]$$
Eq. (114)

where $Q_0$, $W_0$, $f_0$, $g_0$, $W_{L+1}$, $Q_{L+1}$, $f_{L+1}$ and $g_{L+1}$ are as defined in section II, $V_0 = (1/n_I^2)W_0 Q_0$ and $V_{l+1} = (1/n_{II}^2)W_{L+1}Q_{L+1}$.

Applications of boundary conditions for the electric field and magnetic field at $z=z_l$ (l=0, ..., L) yield a recursion relation given in Eq. (36). Rest part of the calculation can be carried out in the exactly same manner as in the TE mode. We end this section with a comment on the inversion matrix of $W_l$ appearing in $M_l^{\pm}$.

Although $E_l$ and $B_l$ are symmetric matrixes, the product $E_l B_l$ is not a symmetric one in general. Thus, the eigenvectors $w_m^{(l)}$ (m=-N, ..., N) of $E_l B_l$ are not orthogonal, i.e., $[w_m^{(l)}]$ $^T w_n^{(l)} \neq 0$ for $m \neq n$. Thus, in this case, $W_l^T W_l$ cannot be expressed as a unit matrix I by the proper normalization. Instead, since $W_l^T E_l^{-1} W_l$ can be a diagonal matrix, it can be normalized as $W_l^T E_l^{-1} W_l = I$. In TM mode, $W_l^T E_l^{-1}$ instead of $W_l^{-1}$ may be used.

VII. Calculation of G(z,z'): TM Mode

If z locates inside the layer l, Eq. (95) becomes $$\left[\frac{1}{k_0^2}\frac{\partial^2}{\partial z^2} - E_l B_l\right]G(z-z') = -\delta(z-z')I \quad \text{Eq. (115)}$$

In this section, we omit, as in sections II and VI, the superscript [0] used to indicate the relevant quantities in the zeroth order periodic structure. For a given layer l, $E_l$ and $B_l$ are not functions of z any more. Except for $W_l$ and $Q_l$ being the matrices constructed from eigenvectors and eigenvalues of $E_l B_l$, the solutions to Eq. (115) are of the same form as Eq. (45) in the TE mode, with the same expressions for $f_{ll'}^{\pm}(z')$ and $g_{ll'}^{\pm}(z')$. In this section, $W_l$ and $Q_l$ are exactly the same as those obtained in section VI. The solutions in the incident medium denoted as region I and the substrate denoted as region II are of the same form as defined in Eq. (46).

VIII. Numerical Implementation: TM Mode

A. Calculation of $U_y(z)$:

To enhance accuracy of the numerical calculation, when an interpolation formula for $U_y(z')$ similar to Eq. (66) is used and analytic integrations are carried out, the discretization of the Lippmann-Schwinger equation [Eq. (97)] can be done as follows:

$$U_y(z_{l-1}) - U_y^{[0]}(z_{l-1}) = \quad \text{Eq. (116)}$$

$$\sum_{j=0}^{l-2}\{\Theta_{l-1,j}^{(+)}K_x\tilde{Y}_{j+1}K_x + \Delta_{l-1,j}^{(+)}Y_{j+1}\}U_y(z_j) +$$

$$\sum_{j=l-1}^{L-1}\{\Theta_{l-1,j}^{(-)}K_x\tilde{Y}_{j+1}K_x + \Delta_{l-1,j}^{(-)}Y_{j+1}\}U_y(z_j) +$$

$$\sum_{j=1}^{l-1}\{\Theta_{l-1,j}^{(+)}K_x\tilde{Y}_j K_x + \bar{\Delta}_{l-1,j}^{(+)}Y_j\}U_y(z_j) +$$

$$\sum_{j=l}^{L}\{\Theta_{l-1,j}^{(-)}K_x\tilde{Y}_j K_x + \bar{\Delta}_{l-1,j}^{(-)}Y_j\}$$

$U_y(z_j)$ for $l = 2, \ldots, L-1$ $$U_y(z_0) - U_y^{[0]}(z_0) = \quad \text{Eq. (117)}$$

$$\sum_{j=0}^{L-1}\{\Theta_{0,j}^{(-)}K_x\tilde{Y}_{j+1}K_x + \Delta_{0,j}^{(-)}Y_{j+1}\}U_y(z_j) +$$

$$\sum_{j=1}^{L}\{\Theta_{0,j}^{(-)}K_x\tilde{Y}_j K_x + \bar{\Delta}_{0,j}^{(-)}Y_j\}U_y(z_j)$$

$$U_y(z_{L-1}) - U_y^{[0]}(z_{L-1}) = \quad \text{Eq. (118)}$$

$$\sum_{j=0}^{L-2}\{\Theta_{L-1,j}^{(+)}K_x\tilde{Y}_{j+1}K_x + \Delta_{L-1,j}^{(+)}Y_{j+1}\}U_y(z_j) +$$

$$\{\Theta_{L-1,L-1}^{(-)}K_x\tilde{Y}_L K_x + \Delta_{L-1,L-1}^{(-)}Y_L\}U_y(z_{L-1}) +$$

$$\sum_{j=1}^{L-1}\{\Theta_{L-1,j}^{(+)}K_x\tilde{Y}_j K_x + \bar{\Delta}_{L-1,j}^{(+)}Y_j\}U_y(z_j) +$$

$$\{\Theta_{L-1,L}^{(-)}K_x\tilde{Y}_L K_x + \bar{\Delta}_{L-1,L}^{(-)}Y_L\}U_y(z_L)$$

$$U_y(z_L) - U_y^{[0]}(z_L) = \quad \text{Eq. (119)}$$

$$\sum_{j=0}^{L-1}\{\Theta_{L,j}^{(+)}K_x\tilde{Y}_{j+1}K_x + \Delta_{L,j}^{(+)}Y_{j+1}\}U_y(z_j) +$$

$$\sum_{j=1}^{L}\{\Theta_{L,j}^{(+)}K_x\tilde{Y}_j K_x + \bar{\Delta}_{L,j}^{(+)}Y_j\}U_y(z_j)$$

Eqs. (116), (117), (118) and (119) can be put together in an expanded matrix form of a system of linear equations:

$$\mathbb{U} - \mathbb{U}^{[0]} = [\mathbb{G}\mathbb{Y}'_+ \bar{\mathbb{G}}\bar{\mathbb{Y}}'_+ \mathbb{H}\mathbb{Y}_+ \bar{\mathbb{G}}\mathbb{Y}'] \quad \text{Eq. (120)}$$

where $\mathbb{U}$, $\mathbb{U}^{[0]}$ are column vectors of dimension L+1 with layer components $U_y(z_l)$ and $U_y^{[0]}(z_l)$, respectively, being still column vectors of dimension (2N+1) with coupled-wave basis components. $\mathbb{G}$, $\bar{\mathbb{G}}$, $\mathbb{Y}$, $\bar{\mathbb{Y}}$ are as defined in Eqs. (73), (74), (75) and (76). $\mathbb{H}$, $\bar{\mathbb{H}}$, $\mathbb{Y}'$, $\bar{\mathbb{Y}}'$ are square matrices with $(L+1)^2$ layer components, each layer component being square matrices with $(2N+1)^2$ components in coupled-wave basis:

$$\mathbb{H}_{lm} = \begin{cases} \Delta_{lm}^{(+)} & \text{for } l > m, m \neq L \\ \Delta_{lm}^{(-)} & \text{for } l \leq m, m \neq L \\ 0 & \text{for } m = L \end{cases} \quad \text{Eq. (121)}$$

$$\bar{\mathbb{H}}_{lm} = \begin{cases} 0 & \text{for } l = 0 \\ \bar{\Delta}_{lm}^{(+)} & \text{for } l \neq 0, l \geq m \\ \bar{\Delta}_{lm}^{(-)} & \text{for } l \neq 0, l < m \end{cases} \quad \text{Eq. (122)}$$

$$\mathbb{Y}'_{lm} = \begin{cases} K_x\tilde{Y}_{l+1}K_x\delta_{lm} & \text{for } l \neq L \\ 0 & \text{for } l = L \end{cases} \quad \text{Eq. (123)}$$

$$\bar{\mathbb{Y}}'_{lm} = \begin{cases} 0 & \text{for } l = 0 \\ K_x\tilde{Y}_l K_x\delta_{lm} & \text{for } l = \neq 0 \end{cases} \quad \text{Eq. (124)}$$

Similarly to the TE mode, we can obtain corresponding formulas for case 1, case 2, case 3 and case 4.

The matrix equation of Eq. (120) can be solved by using the iteration method with an initial setting $\mathbb{U} = \mathbb{U}^{[0]}$ as in the case of the TE mode.

B. Calculation of $g_0$ and $f_{L+1}$

The reflectivity column vector $g_0 = (\rho_{-N}, \ldots, \rho_{-1}, \rho_0, \rho_1, \ldots, \rho_N)^T$ can be extracted as follows:

$$g_0 = g_0^{[0]} + \quad \text{Eq. (125)}$$

$$\sum_{l=0}^{L}\sum_{m=0}^{L}[\mathbb{G}_{0l}\mathbb{Y}'_{lm} + \bar{\mathbb{G}}_{0l}\bar{\mathbb{Y}}'_{lm} + \mathbb{H}_{0l}\mathbb{Y}_{lm} + \bar{\mathbb{H}}_{0l}\bar{\mathbb{Y}}_{lm}]\mathbb{U}_m$$

where $g_0^{[0]}(\rho_{-N}^{[0]}, \ldots, \rho_{-1}^{[0]}, \rho_0^{[0]}, \rho_1^{[0]}, \ldots, \rho_N^{[0]})^T$ is the zeroth order reflectivity column vector.

The reflectivity of a principal order reflection can be obtained by extracting $\rho_0 = (g_0)_0$, Similarly, the transmittance column vector $f_{L+1}=(\tau_{-N}, \ldots, \tau_{-1}, \tau_0, \tau_1, \ldots, \tau_N)^T$ is given as:

$$f_{L+1} = f_{L+1}^{[0]} + \sum_{l=0}^{L}\sum_{m=0}^{L}[\mathbb{G}_{Ll}\mathbb{Y}'_{lm} + \mathbb{G}_{Ll}\mathbb{Y}'_{lm} + \mathbb{H}_{Ll}\mathbb{Y}_{lm} + \mathbb{H}_{Ll}\tilde{\mathbb{Y}}_{lm}]U_m \quad \text{Eq. (126)}$$

where $f_{L+1}^{[0]}=(\tau_{-N}^{[0]}, \ldots, \tau_{-1}^{[0]}, \tau_0^{[0]}, \tau_1^{[0]}, \ldots, \tau_N^{[0]})^T$ is the zeroth order transmittance column vector, and $\tau_O=(f_{L+1})_O$ is the transmittance of the principal order transmission.

The above-described calculated reflectivity and transmittance of each of the TE mode and TM mode are compared with the measured reflectivity and transmittance. The comparison results can be applied to the nondestructive analysis of various periodic structures, for example, holographic grating structures, surface relief and multilayer grating structures, plane dielectric or absorptive holographic grating structures, random sectional dielectric and absorptive surface relief grating structures, two-dimensional surface relief grating structures, or anisotropic grating structures.

The invention has been described using preferred exemplary embodiments. However, it is to be understood that the scope of the invention is not limited to the disclosed embodiments. On the contrary, the scope of the invention is intended to include various modifications and alternative arrangements within the capabilities of persons skilled in the art using presently known or future technologies and equivalents. The scope of the claims, therefore, should be accorded the broadest interpretation so as to encompass all such modifications and similar arrangements.

The invention claimed is:

1. A method of determining physical properties of a multilayered periodic structure, comprising steps of:
   (a) illuminating a real periodic structure and performing at least one of (i) measuring at least one of reflectivity or transmittance of the real periodic structure in response to the illumination or (ii) measuring at least one physical property related to reflectivity or transmittance of the real periodic structure;
   (b) performing at least one of (i) calculating at least one of reflectivity or transmittance of a virtual periodic structure corresponding to the real periodic structure in response to the illumination or (ii) calculating at least one physical property related to at least one of reflectivity or transmittance of the virtual periodic structure in response to the illumination,
   by setting the virtual periodic structure having a repeated shape, one-dimensionally, two-dimensionally or three-dimensionally and at least a horizontally repeating period and a plurality of vertically stacked layers including middle layers among the vertically stacked layers, wherein at least three substances occur in each horizontally repeated period, and
   by calculating physical properties related to the reflectivity and the transmittance of the virtual periodic structure by using a refractive index of each of the at least three substances forming the virtual periodic structure; and
   (c) comparing the at least one physical property related to the reflectivity and the transmittance being measured in the step (a) with the corresponding at least one physical property related to the at least one of reflectivity or transmittance being calculated in the step (b).

2. The method of claim 1, wherein the step (b) is performed by steps including:
   dividing the virtual periodic structure into a zeroth order periodic structure and a perturbed virtual periodic structure obtained by geometrically or physically changing the zeroth order periodic structure in a perturbation region;
   calculating physical properties related to at least one of reflectivity or transmittance of light incident on the zeroth order periodic structure;
   obtaining the physical properties related to at least one of the reflectivity or the transmittance of the perturbed virtual periodic structure by using an approximation algorithm together with the calculated physical properties related to at least one of reflectivity or transmittance.

3. The method of claim 1, wherein the physical properties related to the at least one of the reflectivity or the transmittance being measured in the step (a) are physical properties related to at least one of amplitude or phase of a reflected wave or a transmitted wave in a TE mode electric field and physical properties related to amplitude or phase of a reflected wave or a transmitted wave in a TM mode magnetic field, and the at least one of the reflectivity or the transmittance being calculated in the step (b) are the at least one of the amplitude or phase of the reflected wave or the transmitted wave in the TE mode electric field and the amplitude or phase of the reflected wave or the transmitted wave in the TM mode magnetic field.

4. The method of claim 1, wherein the step (b) comprises steps of:
   expanding a dielectric function in the virtual periodic structure in Fourier series;
   expanding the incident wave, reflected wave and transmitted wave of the beam being incident on the virtual periodic structure in a sum of a plane wave of an electromagnetic wave; and
   calculating the reflectivity and the transmittance by using boundary conditions of expansion coefficients.

5. The method of claim 1, wherein the virtual periodic structure comprises a ridge region formed between groove regions being formed of a third substance, and the ridge region comprises a center part formed of a first substance and a surface layer formed of a second substance on the surface of the center part.

6. The method of claim 5, wherein the surface layer includes at least one of a layer selected from the group consisting of an oxide layer, a coating layer, or a surface roughness layer.

7. The method of claim 5, wherein the third substance has at least one of a gaseous, liquid or solid phase.

8. The method of claim 5, wherein the step (b) comprises expanding the dielectric function of each vertically stacked layer of the virtual periodic structure in the Fourier series, and the expansion coefficient of the Fourier series in each such layer of the virtual periodic structure is expressed by using a complex refractive index of each of the first substance and second substance forming the ridge region and the third substance forming the groove region, a ratio $f_l$ of the region occupied by the first and second substances of each layer l with respect to a period $\Lambda$, a ratio $2\delta_l/\Lambda$ of the region occupied by the second substance only, and a parameter $t_l$ indicating how far the center of the layer l is off from the center of layer 1 of the divided layers in x direction.

9. The method of claim 5, wherein the first substance is formed of at least two or more different substances being horizontally or vertically positioned.

* * * * *